United States Patent [19]

Webb et al.

[11] Patent Number: 5,650,300

[45] Date of Patent: Jul. 22, 1997

[54] METHOD OF PRODUCING MONOCLONAL ANTIBODIES TO ONCOFETAL PROTEIN

[75] Inventors: Thomas E. Webb, Columbus; Paul C. Stromberg, Westerville; Dorothy E. Schumm, Patriot, all of Ohio

[73] Assignee: The Ohio State University, Columbus, Ohio

[21] Appl. No.: 452,252

[22] Filed: May 26, 1995

Related U.S. Application Data

[63] Continuation of Ser. No. 222,201, Apr. 1, 1994, Pat. No. 5,532,159.

[51] Int. Cl.$^6$ .............................. C12P 21/08; C12N 5/12; C07K 16/18; C07K 16/30
[52] U.S. Cl. ........................... 435/70.21; 435/172.2; 435/330; 435/344; 530/388.25; 530/387.1; 530/388.1; 530/388.8
[58] Field of Search ........................ 530/388.1, 388.25, 530/388.8, 387.1; 435/240.27, 70.21, 172.2

[56] References Cited

U.S. PATENT DOCUMENTS

| | | | |
|---|---|---|---|
| 4,746,539 | 5/1988 | Webb et al. | 424/85 |
| 4,871,661 | 10/1989 | Webb et al. | 435/7 |
| 5,310,653 | 5/1994 | Hanausek-Walazek et al. | 435/7.23 |

OTHER PUBLICATIONS

Steve Runge's thesis "Characterization of an Oncofetal Protein (OFP) and Cloning of its cDNA" pp. 76–113, Cataloged at Ohio State University, Jul. 30, 1992.

Oredipe, O.A., et al. Carcinogenesis, 10(12): 2175–2181, Dec., 1989.

Abstract #1711, Schumm, D.E., Proc. Ann. Meet. Am.Assoc. Ca. Res. 33:A1711, Mar. 1992.

Abstract #1515, Schumm, D.E., et al. "Characteristics of an Oncofetal Tumor Marker Protein", Proc. Am. Assoc. Ca. Res. 31: 256, Mar. 1990.

Abstract #1669, Runge, S.W., et al., "Characterization of an Oncofetal Protein (OFP) and Cloning of Its cDNA", Proc. Am. Assoc., Ca. Res. 32: Mar. 1991.

Abstract #7502, Runge, S.W., et al. "Characterization of an Oncofetal Protein (OFP) and Cloning of Its cDNA", 75th Annual Meeting of Assoc. of Biochem. and Mol. Biol. FASEB, Apr. 1991.

Runge, S., et al. "Development and Use of Monoclonal Antibodies Against an Oncofetal Protein Associated with Carcinogenesis and Tumorgenesis" Immunlogical Investigation, 20(3):269–286 (1991).

Stromberg, Paul C., et al. "Expression of an Oncofetal Protein (OFP) in Rat and Human Leukemia Cells", Leukemia Research, vol. 15, pp. 427–433 (1991):

*Primary Examiner*—James C. Housel
*Assistant Examiner*—Susan A. Loring
*Attorney, Agent, or Firm*—Calfee Halter & Griswold

[57] ABSTRACT

The present invention provides a low cost, less toxic, anti-cancer immunotherapy which enhances the host's immune system ability to destroy or contain cancers, and also provides a diagnostic test for cancer. Specifically, the present invention provides monoclonal antibodies specific for, that is, specifically bind, oncofetal protein (OFP), a cancer cell product. Tumors treated with a single dose of the monoclonal antibodies against OFP are markedly reduced in size, and leukemic populations of cells treated with a single does of monoclonal antibodies against OFP are significantly decreased in number. Since the monoclonal antibodies of the present invention do not bind to tumor cells, the monoclonal antibody treatment overcomes the disadvantages associated with tumor cell targeting. Monoclonal antibodies to OFP offer a simple and inexpensive agent for use as a primary or adjuvant therapy against a wide variety of cancers and tumors in humans and other animals. The monoclonal antibodies against OFP are also employed to detect cancer in animal, including human patients.

10 Claims, 7 Drawing Sheets

METHOD OF PRODUCING MONOCLONAL ANTIBODIES TO ONCOFETAL PROTEIN

This is a continuation of application(s) Ser. No. 08/222, 201 filed on Apr. 1, 1994, now U.S. Pat. No. 5,532,159.

BACKGROUND OF THE INVENTION

Mammalian cells that have undergone malignant transformation, that is, are "cancerous", bear chemical markers that potentially allow recognition by the host's own immune system. Nevertheless, the host's immune system frequently fails to recognize and/or eliminate cancer cells. Despite chemotherapy and/or surgery, the cancer may kill the host.

Attempts have been made to enhance the immune system's natural antitumor potential by various immunotherapy treatments. Immunotherapies are typically used in conjunction with surgery and/or chemotherapy. Certain immunotherapies involve administering biological. response modifiers including, for example: tumor necrosis factor (hereinafter "TNF"), which includes two closely related molecular species TNF-$\beta$, also known as lymphotoxin, and TNF-$\alpha$, also known as cachectin, which directly kill certain types of tumor cells; -interferon which activates T cells, natural killer cells and inhibits the growth of certain tumor cells; and $\alpha$-interleukin-2, which increases the proliferation of antigen specific cytotoxic T-cells, B cells, natural killer cells and activates lymphokine-activated killer cells. Interleukin-2 has demonstrated limited effectiveness alone even at high dosages. However, interleukin-2 treatment is toxic to the patient, and is currently recommended only for patients for whom no other treatment is available.

TNF-$\beta$, produced by activated macrophages and lymphocytes, is a potent mediator of natural killer cells, lymphokine-activated killer cells and cytotoxic lymphocyte activity. In addition, TNF is cytotoxic and cytostatic to tumor cells. Several cytokines interact synergistically with TNF. Administration of TNF has prolonged the survival of leukemia patients, resulted in the regression of various solid tumors and demonstrated potential efficacy in the treatment of various cancers such as bladder and gastrointestinal cancer. While interleukin 2 and TNF show promise in the treatment of cancer, they are relatively non-specific effector cytokines with a wide range of activities, some of which cause undesirable toxic side effects at therapeutic doses.

A problem with administering biological response modifiers is that the modifier, particularly when given in high continuous doses, is expensive, may require multiple treatments, may produce only marginal results and has toxic side effects.

Other immunotherapy methods involve the removal and manipulation of host cells or fluids. Removal of peripheral blood cells and treatment with interleukin-2 has increased their tumoricidal capability by stimulating the activity of natural killer cells and lymphokine activated killer cells. Immunodepletive therapy of patient's plasma and bone marrow has been employed to remove blocking factors or to add tumoricidal factors. However, these treatments are time consuming, complex, costly and often ineffective. As with administration of interleukin-2 and TNF, there are serious toxic effects in many patients.

Passive immunotherapy using monoclonal antibodies, directed to cancer cell antigens, has been employed to initiate cancer cell destruction via the host's immune system and offers great potential in the treatment of cancer. However, the promise of monoclonal antibodies depends upon their binding to a unique antigen on the surface of the cancer cell. It is rare that these cell surface antigens or epitopes thereof are unique to the cancer cell. In addition, low surface density of the cancer cell surface antigen, low affinity of the monoclonal antibody for the antigen and poor antibody uptake by the cancer cell are serious problems. Partially for these reasons, no therapy with simple monoclonal antibody has ever caused tumor regression. The most successful monoclonal antibody treatments depend on conjugating the antibody with a cytotoxic drug or radioisotope. While treatments such as these show considerable promise, there are still toxic side effects.

To date no single treatment cures cancer, and thus it is desirable to increase the immunotherapy arsenal against cancer. It is particularly desirable to have a low cost, less toxic, anti-cancer immunotherapy which enhances the host's immune system ability to destroy or contain cancer.

In addition to treating cancers it is also desirable to have a noninvasive diagnostic test that detects the presence of cancer. Currently cancer is detected primarily by imaging techniques such as x-ray, CAT scan and NMR.

CAT scan and NMR procedures are moderately expensive and are typically employed when the patient's symptoms warrant an investigation into the cause. Thus, where a patient is asymptomatic a cancer may grow undetected.

While chest x-rays may be used fairly routinely to diagnose lung cancer and mammograms have been recommended in some cases, the x-ray is limited in scope and will not alert a physician to the presence of other cancers. Moreover, x-rays expose a patient to radiation which is carcinogenic and are thus used only in subjects at high risk for cancer.

It would be desirable to have a general inexpensive routine diagnostic test for cancer that does not employ radiation which is capable of detecting the presence of cancer and thereby alerting the physician and patient to the need for further examination.

SUMMARY OF THE INVENTION

The present invention provides a low cost, less toxic, anti-cancer immunotherapy which enhances the host's immune system's ability to destroy or contain cancers, and the present invention also provides a diagnostic test for cancer. Specifically, the present invention provides monoclonal antibodies specific for, that is, specifically bind, oncofetal protein, (hereinafter "OFP"), a cancer cell product. OFP is unique in that OFP is not a structural protein or antigen on the cancer cell surface, rather it is secreted from the cancer cell. Tumors treated with a single dose of the monoclonal antibodies against OFP are markedly reduced in size, and leukemic populations of cells treated with a single dose of monoclonal antibodies against OFP are significantly decreased in number. Since the monoclonal antibodies of the present invention do not bind to tumor cells, the monoclonal antibody treatment overcomes the disadvantages associated with tumor cell targeting. It is believed that OFP is immunosuppressive and by sequestering or removing OFP via the monoclonal antibody, the patient's immune defense against tumors is released from impairment allowing a more efficient and natural rejection of the cancer. Monoclonal antibodies to OFP offer, a simple and inexpensive agent for use as a primary or adjuvant therapy. Moreover, because monoclonal antibodies to OFP do not depend upon binding to a specific tumor cell type, they are effective against a wide variety of cancers and tumors in humans and animals. The monoclonal antibodies against OFP are also employed to detect cancer in animal patients, including human patients.

DETAILED DESCRIPTION OF THE INVENTION

Figure 1:
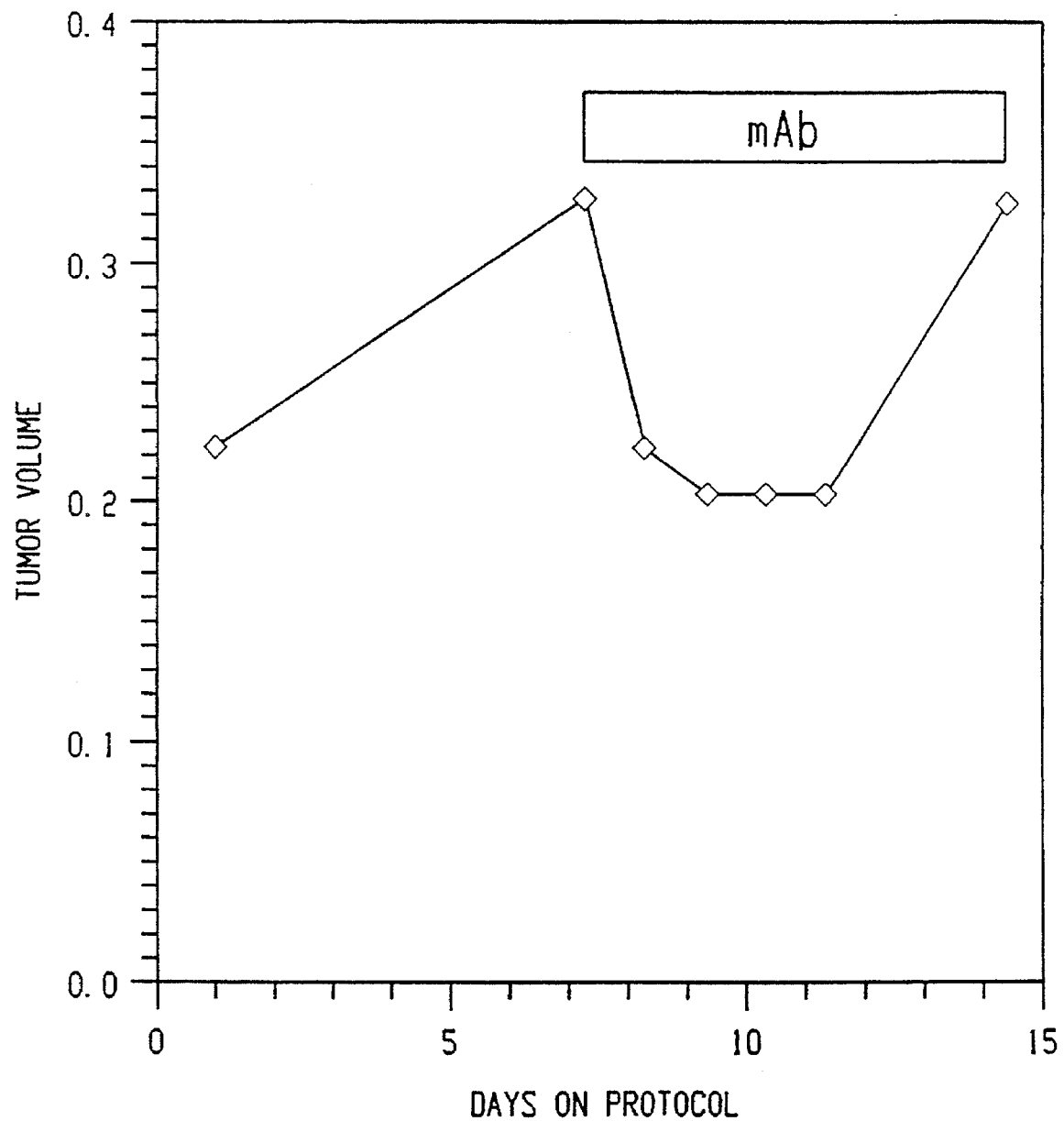
FIG. 1 is graph showing the effect of anti-human OFP monoclonal antibody on the growth rate of a MCF-7 human breast adenocarcinoma transplanted into a six month old NIH Swiss Nude Mouse.

The monoclonal antibodies of the present invention are specific for, that is, specifically bind, OFP secreted by cancers including tumors and leukemias. It is believed that the OFP is immunosuppressive, and by removing OFP circulating in the blood stream via the monoclonal antibodies, a host's immune system is able to attack the tumor more actively. The monoclonal antibodies against OFP decrease the volume of tumors in vivo and decrease the number of cancer cells n vitro. The monoclonal antibodies provided by the present invention are also useful for the treatment, diagnosis and study of cancers, particularly tumors, including mammalian tumors, particularly human breast tumors.

Oncofetal protein (hereinafter also referred to as "OFP") is released into the circulation from pre-malignant lesions or foci, and from malignant tumors beginning during the early stages of tumor development (Oredipe, O. A., et al. *Carcinogenesis* 10:2175–2181, 1989). OFP is also produced in leukemia cells (Stromberg, P. C., et al. Leukemia Research 15:427–433, 1991). However, OFP is not produced by benign tumors, nor is it produced by non-cancerous cells except fetuses (Oredipe, et al. Carcinogenesis 10:2175–2181, 1989; Stromberg, et al., Leukemia Research, 15:427–433, 1991 and Schumm, D. E. and Webb, T. E., Cancer Res. 11:401–406, 1984). However, although OFP is retained in significant concentration in fetuses and placenta, it is not released to maternal circulation. Thus, because OFP is only present in a patient's circulation if cancer is also present in the patient, monoclonal antibodies which detect the presence of OFP concomitantly detect cancer.

Similarly, monoclonal antibodies to OFP are useful in monitoring the progress of cancer treatment. For example, if OFP is detected in the patient after anticancer treatments then further treatments are necessary.

Production of Monoclonal Antibody

Isolation of Rat OFP

Rat OFP was purified from the blood of a DMBA induced tumor-bearing Sprague-Dawley rat. Blood was collected from primary mammary tumor bearing rats, pooled and fractionated with ammonium sulfate. The protein fraction that precipitated between 30 and 60% saturation of the aqueous ammonium sulfate solution, which fraction was found to contain all the RNA-releasing activity/OFP, was dissolved in approximately 5 ml of a solution containing tris(hydroxymethyl amino)methane/potassium chloride/magnesium chloride buffer having a pH of about 7.5, and 0.1M potassium chloride (TMK buffer-0.1M KCl) then dialyzed, at a pH of about 7 to 8, overnight against the same buffer. An aliquot of the dialyzed solution containing approximately 300 mg of total protein was applied to a 3.0×90 cm column of cross-linked hydrophobic agarose molecular sieve resin, available commercially from a variety of sources under the trade name Sepharose CL-6B. The column was eluted with the TMK buffer-0.1MKCL and 6 ml fractions were collected.

The fractions which eluted from the molecular sieve column at a molecular weight of 40,000–70,000 were further purified by chromatography in order to remove albumin. A sample containing 25.0 mg of OFP in the TMK buffer-0.1M KCl was loaded onto a 1.0×10.0 cm column containing CM Affi-Gel Blue, available from Bio-Rad Lab., Richmond, Calif. and eluted with 0.4M potassium chloride-TMK buffer. Subsequent dialysis of the eluate and electrophoresis on sodium dodecylsufate-polyacrylamide gel confirmed that the chromatography essentially removed albumin.

Further purification was accomplished by the following affinity chromatography technique. The single stranded DNA column (3.5×9.0 cm) designated D-8273, available from Sigma Chemical Co., St. Louis, Mo., was equilibrated with 50 mM NaCl-TMK equilibrating buffer (TMK=50 mM Tris-HCl, pH 7.5–25 mM KCl-2.5 mM $MgCl_2$) and the active protein fractions eluted from the CM Affi-Gel Blue column were applied to the single stranded DNA column in equilibrating buffer containing 1.0 mM dithiothreitol. The active protein fractions were recycled through the column twice, then the column was washed with 50 mM NaCl-TMK buffer, and then the oncofetal RNA transport factor was eluted with 2.0M NaCl-TMK buffer. The eluted factor was dialyzed against TMK buffer, then concentrated using Centriprep Concentrators from Amicon, Beverly, Mass. Prior to the production of monoclonal antibodies to OFP, the OFP was quantified using the Bioassay hereinafter described. Therafter, the rat OFP was then quantified using a competition ELISA or immunobioassay. The purity of OFP obtained by this method ranges from 85–98% for different preparations. The OFP separates into 2 bands on Western Blots, a band at from about 49 to about 51 kD and a band at from about 54 to about 56 kD. The protein phosphorylated at tyrosine residues.

The purified OFP thus obtained was used to produce antibody-containing serum in mice. These mice served as spleen cell donors for hybridoma production.

Isolation of Human OFP

Human OFP was isolated and purified from human placenta. Although less preferable, it may be isolated and purified from the blood serum of a cancer patient. The human placenta was homogenized in 1.5 ml/gm of TMK-sucrose (50 mM Tris-HCl, pH 7.5–25 mM KCl-2.5 mM MgCl2-0.25M sucrose) using 1 stroke with a rotating loose pestle and 5 strokes with a rotating tight pestle. For every 10 g of placenta, 10 μl of 100 mM phenylmethylsulfonyl fluoride, a protease inhibitor in ethanol was added before homogenizing. All procedures were done at 0°–4° C. The homogenate was centrifuged for 10 min. at 10,000 rpm and the supernatant was recentrifuged at 40,000 rpm (100,000 g) for 90 minutes. The 100,000 g supernatant was fractionated with ammonium sulfate. First, the supernatant was brought to 30% saturation with $(NH_4)_2SO_4$ by slow addition of 1.87 gm/10 ml. The mixture was centrifuged at 10,000 rpm for 10 minutes and the supernatant was adjusted to 60% saturation with $(NH_4)_2SO_4$ by adding a further 1.66 gm/10 ml supernatant. The mixture was centrifuged for 10 minutes at 10,000 rpm and the pellet containing OFP was resuspended in TMK and dialyzed against 0.1M KCl-TMK buffer, pH 7.5. At this stage the protein concentration is 50–60 mg/ml. Next, 3.0 ml of the dialyzed preparation was passed through a Sepharose 6B-Cl column (3.0 cm×90 cm), and 3.0 ml fractions were collected. A bioassay (as hereinafter described) based on enhancement of RNA release from isolated rat liver nuclei was used to identify fractions containing OFP. The fractions containing OFP were combined. The combined fractions contained 6–8 mg of protein/ml. The sample was adjusted to 20 mM Tris-HCl pH 8.0 by dialyzing overnight. The dialyzed sample was passed over a Mono-Q (HR 5/5) column on an FPLC system from Pharmacia-LKB, Piscataway, N.J. The protein bound to the cation exchange column was eluted with a linear NaCl (0.0–1.0M) gradient.

The bioassay, based on enhancement of RNA release from rat liver nuclei, was again used to identify fractions containing human OFP. Each 10 ml sample, containing approximately 3.0 mg protein/ml, of dialyzed preparation from the Mono Q column was next passed over a single stranded calf thymus DNA (25 g)-cellulose column from Sigma Chem. Co., St. Louis, Mo. which was pre-equilibrated with 50 mM NaCl-TMK. The column containing the sample was washed with 50 mM NaCl-TMK, then the bound OFP was eluted with 40 ml of 2.0M NaCl-TMK buffer, pH 7.5. Fractions were collected and the column eluate was monitored at 280 nm with a UV-monitor to detect the peak of protein eluted. The eluate from the DNA cellulose column was concentrated and the buffer was changed from 2.0M NaCl-TMK to phosphate buffered saline by repeated centrifugation and reconstitution with phosphate buffered saline in centricon filters available from Amicon Inc., Beverly, Mass. The phosphate buffered saline contains: 137 mM NaCl, 2.7 mM KCl, 20 mM $Na_2HPO_4$, 1.0mM $KH_2PO_4$ at a pH of 7.4. The final OFP concentration after a 20-fold volume reduction was approximately 0.2 mg/ml and OFP activity was confirmed by the bioassay using rat liver nuclei. The human placental OFP separates into 2 bands on Western Blots, a band at from about 49 to about 51 kD and a band at from about 54 to about 56 kD. The MOFPE which binds to rat and human tumor derived OFP does not bind to the human placental OFP.

The oligosaccharide moiety of the human placental OFP was examined using known lectins having an affinity for specific oligosaccharides. The oligosaccharides on the OFP were identified by use of a biotinylated lectin kit which employs avidin conjugated horseradish peroxidase, from Vector Labs, Burlingame, Calif. The lectins are tested using the Western blot technique. The results are presented below in Table A.

TABLE A

Identification of Oligosaccharide Moiety on OFP using Biotinylated Lectins or Antibody on Western Blots

| Type of Lectin or Antibody | Specificity of Lectin or Antibody for Oligosaccharide Residue | Rat Tumor Plasma | Rat Fetal Cytosol | Human Placental Cytosol | Human Tumor Plasma |
|---|---|---|---|---|---|
| Con A | D-mannose (α-linked in oligosaccharide core) | + | + | + | + |
| WGA | N-acetylglucosamine (sialic acid) | + | – | – | – |
| SWGA | N-acetylglucosamine (not sialic acid) | + | NT | – | – |
| PSA | D-mannose (α-linked with N-acetylchitobiose linked α-fucose core) | + | – | – | + |
| LCA | D-mannose (α-linked in oligosaccharide core) and adjacent | + | – | – | + |
| SJA | N-acetyl-D-galactosamine galactose | – | NT | – | – |
| UEA-I | α-linked fucose | – | NT | – | – |
| SBA | Terminal α or β N-acetylgalactosamine | – | – | – | – |
| DBA | N-acetyl-D-galactosamine | – | + | – | + |
| BSL-I | α-galactose, α-N-acetylgalactosamine | – | – | – | – |
| Anti-phos-pho- | phosphorylated tyrosine residues | + | NT | – | + |

TABLE A-continued

Identification of Oligosaccharide Moiety on OFP using
Biotinylated Lectins or Antibody on Western Blots

| Type of Lectin or Antibody | Specificity of Lectin or Antibody for Oligosaccharide Residue | Reaction with From Different Sources | | | |
|---|---|---|---|---|---|
| | | Rat Tumor Plasma | Rat Fetal Cytosol | Human Placental Cytosol | Human Tumor Plasma |
| tyrosine monoclonal antibody | | | | | |

NT - not tested
Con A - concanavalin A
WGA - wheat germ agglutinin
LCA - lens culinaris; LCA recognizes additional sugars besides D-mannose as part of the binding site; thus LCA has a narrower specificity then Con A.
PSA - Pisum sativum agglutinin
SBA - soybean agglutinin
DBA - Dolichos bifloris agglutinin
UEA-I - Utex earopeus agglutinin I
BSL-I - Bandeiraea simplicifolia (lectin I)
SJA - Sophora japonica agglutinin
SWGA - succinylated wheat germ agglutinin As can be seen from Table A, of the lectins studied, the OFP from human placenta binds only Con A. In contrast, the both human and rat tumor generated OFP bind additional lectins. Specifically, OFP from human tumors, in addition to Con A, binds PSA, LCA, and DBA. Rat tumor OFP, in addition to CON A, binds WGA, SWGA, PSA and LCA. Such differences in lectin binding are due to differences in the structure of the OFP oligosaccharide. It appears that the oligosaccharide on rat tumor OFP from Hepatoma 7777 bearing rats is a complex highly branched structure, containing D-mannose α-linked oligosaccharide core, N-acetyl glucosamine, sialic acid, D-mannose α-linked in oligosaccharide core, and D-mannose, α-linked with N-acetyl chitobiose linked α-fucose core. In contrast, the OFP from human placental cytosol was positive for only D-mannose that is α-linked in oligosaccharide core.

Also, characterization of the human placental OFP with anti-phosphotyrosine monoclonal antibodies established that the human placental OFP is not phosphorylated with tyrosine residues. Thus the tumor produced OFP differs among species, that is it differs among humans and rats. Furthermore, the OFP from placenta is structurally different from the OFP produced from tumors.

Isolation of Canine OFP

Canine OFP was isolated and purified from canine placenta by the same procedure as outlined above for isolation of human OFP. Activity was identified by the immunobioassay.

Preparation of Anti-Rat Monoclonal Antibodies

For primary immunization, male Balb/c mice were injected subcutaneously on the back with 20 mg rat OFP (40 μg/ml) in Complete Freund's Adjuvant (0.5 vol) and phosphate-buffered saline (0.5 vol.). Intraperitoneal booster injections of 15 μOFP in PBS were given on days 21 and 42. On day 63, the mouse spleens were harvested and a suspension of spleen cells were prepared. The spleen cells were then fused with a Balb/c myeloma cell line P3×63/Ag 8.653, according to the method of G. Galfre, C. Milstein in *Methods in Enzymoloy*, Acad. Press, New York, pp. 7343–46, 1981.

Viable spleen cells were obtained by disrupting the spleen using limited homogenization. To a suspension of approximately $2 \times 10^7$ tumor cells and $2.5 \times 10^6$ spleen cells at 37° C. was added PEG (5%; M.W. 1500, Sigmal Chem. Co.). The cells were washed then plated in Dulbeco's Modified Eagles Medium (DMEM) supplemented with 20% fetal calf serum. The cells were fused by incubation of the 2 cell types with 50% polyethylene glycol. Fused tumor-spleen cells were selected in hypoxanthine-aminopterin-thymidine medium. Spleen cells will normally die but some procedure must be used to kill off tumor (myeloma) cells, leaving only hydridomas surviving. On day after fusion the medium was changed to HAT medium (Sigma Chem. Co, St. Louis) which contains aminopterin to inhibit de novo biosynthesis of nucleotides and hypoxanthine and thymidine to by-pass de novo pathway via the salvage pathway to permit growth. The tumor, but not hybridoma cells, lack the salvage enzyme hypoxanthine/guanine phosphoribosyl transferase, and therefore die. The surviving hybridomas contain the enzyme (from the lymphocytes); then the medium was tested for anti-OFP antibody production by the direct ELISA. The hybridomas were cloned to isolate a single antibody producing cell, then to grow this cell line up in bulk. Cloning was by 'limiting dilution' to give theoretically a mean of one cell per well. This procedure, followed each time by culture of the cells, was repeated 3 times to insure a pure cell line. The wells were screened for appropriate monoclonal antibody production by the direct ELISA tests ability of antibody to bind to 96 well plates coated with pure human OFP and by the immunobioassay. The positive clones were identified by direct ELISA, by the immunobioassay designed to detect anti-OFP antibodies and in some cases by Western blot analysis.

Six hybridoma lines were isolated that produce anti-rat OFP monoclonal antibodies and then inoculated into the peritoneum of syngeneic mice for large scale production of monoclonal antibodies. Details of this procedure can be found in Immunochem. in Practice, A. Johnstone, R. Thorpe, Blackwell Sci. Publ., Boston, Mass. In brief, each of the six hybridomas was individually grown in tissue culture medium, then isolated by centrifugation and resuspended in new tissue culture medium at a concentration of $10^7$ cells per ml. For each hybridoma, $5 \times 10^6$ cells were injected into the intraperitoneal cavity of a Balb/c mouse which had been primed one week earlier with 0.5 ml of pristane from Sigma Chemical Co., St Louis, Mo. When the abdomen of each of the 6 mice became distended, the fluid was drained and the cells were-removed by centrifugation. The monoclonal antibodies, present in high concentration in the cell-free ascitic fluid, were purified by passing aliquots of the ascitic fluid through an Affi-Gel Protein A agarose column. The Affi-Gel Protein A agarose column, binding and elution buffers, and detailed instruction for use thereof were provided in an Affi-Gel Protein A MAPS II kit obtained from BioRad Labs, Richmond, Calif.

Three of the monoclonal antibodies, produced by the above procedure, designated MOFPA, MOFPB, and MOFPC are directed to the core protein of the tumor produced OFP and are of the IgG1 class. The three other monoclonal antibodies, directed primarily to an oligosaccaride, that is, carbohydrate moiety of the tumor produced OFP, are designated MOFPD, MOFPE, and MOFPF. The monoclonal antibodies which are directed to the protein, rather than to the carbohydrate moiety, are more effective in reducing tumor volume.

In developing a highly specific antibody against OFP, to be used as a diagnostic agent or a therapeutic agent, it is desirable that the anti-OFP monoclonal antibodies are capable of binding OFP regardless of the type of tumor that produced the OFP. It is also desired that the monoclonal antibody be capable of binding OFP and regardless of the individual who is the source of the OFP.

OFP is a glycoprotein, more specifically a glycophosphoprotein, that is, a protein with some hydroxyl groups on the amino acids esterified with either phosphate or oligosaccharide. Monoclonal antibodies against glycoproteins are often directed, at least in part, against the oligosaccharide moieties of the glycoprotein. The oligosaccharide moiety of the OFP is the more variable portion of the glycoprotein. That is the chemical structure of the oligosaccharide moieties may vary among species, or it even may vary among individuals within a species. The protein of OFP is highly conserved, that is, it does not vary significantly among species. If a monoclonal antibody is directed against an oligosaccharide moiety which is not present on the glycoprotein that one is trying to bind with the monoclonal antibody, the monoclonal antibody may fail to recognize the glycoprotein. Thus, there is a problem regarding the specificity of monoclonal antibodies not directed exclusively against the protein.

Of the 6 anti-rat OFP monoclonal antibody-producing hybridomas produced above, three of these monoclonal antibodies cross-react with human OFP. Two anti-rat monoclonal antibodies, MOFP-D and E, which are directed primarily to oligosaccharide moieties, cross-reacted with OFP obtained from some cancer patients but not other patients. The anti-rat OFP monoclonal antibodies, MOFP-A and B, are directed to protein epitopes of tumor produced OFP; since the protein portion of the OFP varies less among species, these antibodies are the most specific of the anti-rat monoclonal antibodies isolated.

It has been discovered that the OFP present in high concentration in the term placenta, contains much less oligosaccharide than does the tumor produced OFP that was isolated from the plasma of tumor-bearing hosts. OFP from human placental cytosol was positive for only D-mannose that is α-linked in oligosaccharide core. Since placental OFP contains less oligosaccharide than the tumor produced OFP, the monoclonal antibodies obtained against placental OFP are typically very specific for the protein core of OFP. Thus, such monoclonal antibodies are specific for OFP from a wide range of tumors from different species.

Preparation of Anti Human Monoclonal Antibody

A monoclonal antibody directed against the protein core of human OFP, was obtained as above except that purified human OFP from placenta was administered to the mice and the antibodies were purified from the culture medium of the hybridoma. The resulting monoclonal antibodies are very specific for human OFP, and are designated herein as MOFP-HIA9, MOFP-HIB7, MOFP-HIC8, MOFP-HA9, MOFP-HB7 & MOFP-HC8. The latter three monoclonal antibodies were derived from hybridomas prior to the few additional cloning steps used to isolate the 3 pure hybridoma lines which produce MOFP-HIA9, MOFP-HIB7 & MOFP-HIC8. MOFP-HIA9 has been deposited with American Type Culture Collection; 12301 Parklawn Drive, Rockville Md. 20852, on Mar. 3, 1994 the designation number is HB11565. MOFP-HIC8 has been deposited with American Type Culture Collection on Mar. 15, 1994 the designation number is HB11582. When referring herein to monoclonal antibodies against human OFP generally, the designation "MOFP-H" is frequently used.

Preparation of Anti Canine Monoclonal Antibody

The anti canine monoclonal antibodies were prepared as described above for the preparation of the preparation of anti human monoclonal antibody, except that the canine OFP isolated as described above, was used. The resulting monoclonal antibodies are very specific for canine OFP, and are designated herein as MOFP-51C9, MOFP-51E9 and MOFP-51F10. MOFP-51C9 has been deposited on Mar. 11, 1994 with American Type Culture Collection, the designation number is HB11579.

In-Vivo Evaluation of Monoclonal Antibodies to OFP

Applicants have found that there is an appearance and steady increase in the concentration of OFP in the blood and in the target tissue of rats beginning a few days after a carcinogen treatment and transplantation of transplantable tumors (U.S. Pat. No. 4,871,661 to Webb, et al.) into normal rats. While the OFP levels in the target tissue reaches a plateau, the level in the blood undergoes a transient decrease beginning at about 21 days after treatment of 50 day old rats with the carcinogen DMBA (U.S. Pat. No. 4,937,185 to Webb, et. al.). This transient decrease is due to immune clearance by anti-OFP circulating antibodies present during the nadir. Thereafter, the OFP level in the blood is slowly restored to a level 3-fold higher than that attained at 21 days after treatment. The level of blood OFP accelerates upon promotion or when a tumor forms. After removal of the solitary transplantable tumor from a host, the host's blood level of OFP drops to nearly zero.

Mammary Tumors

Mammary tumors were induced by giving 50 day old female Sprague Dawley rats a single, 15 mg dose of 7,12-dimethylbenz(a)anthracene (DMBA) administered by mouth, according to the method of C. G. Huggins, Experimental Leukemia and Mammary Cancer Induction, Chicago, Ill., Univ. Chicago Press, 1979. These rat mammary tumors which develop to usable size in 4–5 months, are an accepted model for human breast cancer (Goldman et al., "Plasma Estradiol and Prolactin Levels and Their Response to Stress in Two Strains of Rat with Different Sensitivities to 7,12-Dimethylbenz(a)-Anthracene-Induced Tumors," Cancer Letters, 25 (1985) pp. 227–282, Elsevier Scientific Publishers Ireland Ltd.)

Tumor volume was calculated from measurements made with micrometer calipers. Tumor size was also determined by magnetic resonance imaging (MRI).

Monoclonal antibodies designated MOFPA were injected in a single 100 μg or 165 μg dose, via the tail vein of tumor bearing rats at varying times, ranging from 4 weeks to 16 weeks after the DMBA was administered. In essentially all cases, the tumor volume decreased within one day after injection of the MOFP-A, as shown in Table 1. Additionally, the tumor volume remained suppressed for the length of the studies, which ranged from 8 to 22 days.

The initial decrease, that is, shrinkage, of tumor volume varied somewhat from experiment to experiment as assessed by micrometer calipers. These variations appear to be due to variations in the amount of fluid accumulated in the tumor, the amount of cell destruction, and monoclonal antibody dosage.

In some studies the tumor volume was measured 5–6 days after treatment and then the tumor was drained of fluid using an 18 gauge hypodermic needle and the tumor volume was remeasured. When fluid was withdrawn from the tumor, a further significant drop is seen in tumor volume as shown in Table 1. No fluid could be withdrawn from tumors of control rats, that is rats not treated with MOFP-A.

After administration of the MOFP-A, the tumor typically had a large fluid-containing cavity surrounded by a mass of necrosis that represented 80–90% of the tumor volume and a small patch of viable tumor representing approximately 10% of the tumor volume. The DMBA-induced rat mammary tumors and the fluid obtained from such tumors was found to contain immune system cells, such as macrophages and lymphocytes, which are believed to cause the destruction of the tumor cells.

To determine if the tumor shrinkage is due to MOFP-A specifically for OFP, rats bearing DMBA-induced mammary tumors were also treated with a mixture of 160 μg MOFPA and 400 μg OFP, so that OFP was present in excess. Such treatment did not inhibit and appeared to accelerate tumor growth as shown in Table 1. This indicates that the inhibition of tumor growth by MOFP-A is specifically due to the MOFP-A antibody.

MOFP-B was also administered in a single dose via the tail vein of the rats bearing measurable mammary tumors (4–5 months post-DMBA). The dosage was either 150 or 165 μg/rat. Small tumors, that is, having a volume of 0.3–0.5cc, or less, in most cases essentially disappeared and did not recur during the period of observation when the rat was treated with 5 μg of MOFP-B. When the tumor was large having a volume of 5.5 cc or greater, the volume of the tumor was reduced by about one half, where it remained for several weeks.

Rats bearing DMBA-induced mammary tumors were also treated with a single dose of 150 or 165 μg of MOFP-B. As shown in Table 1, injecting rats with these dosages of MOFP-B decreased tumor volume. Thus, both MOFP-A and MOFP-B inhibit mammary tumor growth.

The effect of a conventional tumor shrinking agent, tumor necrosis factor-$\alpha$ ("TNF-$\alpha$") on rat mammary tumor volume was compared to the effect of MOFPA and MOFPB. A single, 10 μg dose of TNF-$\alpha$ was administered intravenously to Sprague Dawley strain rats, in which mammary tumors were previously induced by DMBA. The TNF-$\alpha$ caused only a one day, transient interruption between day two and day three following injection of the TNF-$\alpha$. In addition, the percent volume change in rat mammary tumors was only slightly reduced by this treatment, as shown in Table 1. In comparison, the tumors treated with MOFP-A and MOFP-B were significantly reduced. Thus, MOFP-A and MOFP-B are more potent inhibitors of tumor growth than the conventional tumor necrosis factors.

Two nonspecific, that is not specific for OFP, monoclonal antibodies, not within the scope of the present invention, were injected into the tail vein of rats to determine the effect, if any of these two nonspecific monoclonal antibodies on induced rat mammary tumors. These two nonspecific monoclonal antibodies, anti-urease monoclonal antibody and anti-$T_2$ toxin monoclonal antibody, both of the IgG1 class, had little effect on the volume of the rat mammary tumors. As shown in Table 1, there was virtually no change in the percent volume change of rat mammary tumors following these treatments with non-specific monoclonal antibodies. Thus, the tumor shrinkage caused by the MOFP of the present invention is due to the specificity of the MOFP for OFP, rather than a generalized effect.

As shown in Table 2, tumor size determinations by magnetic resonance imaging confirmed the inhibitory effect of MOFP-A on rat mammary tumor growth. The size of each tumor on rats injected with MOFP-A decreased substantially by six days after treatment. In contrast, the size of tumors on an untreated rat increased significantly during the same time period.

Rat Hepatoma Tumors

Four rats received fragments of transplantable rat hepatoma 7777 tumors. 25 days after the tumors were transplanted, that is when the tumors were 1–2 cm in diameter, the rats were injected with a single 170 g dose of MOFP-B. As shown in Table 1, each of the tumors exhibited a significant decrease in the percent volume change after treatment. Thus, MOFP-B initially inhibits the growth of rat hepatoma tumors. The growth resumed at later time periods.

MCF-7 Human Breast Adenocarcinoma

The MCF-7 human breast adenocarcinoma cells were obtained from the American Type Culture Collection, Rockville, Md., and grown in Minimal Essential Medium supplemented with non-essential amino acids, L-glutamine and 10% fetal bovine serum. Approximately $5 \times 10^6$ cells were injected subcutaneously into nude mice. Treatment was initiated when the tumor was measurable with micrometer calipers. When 10 μg of MOFP-HIA9 was administered intraperitoneally to 6 month old NIH Swiss Nude Mice, there was an observable decrease in tumor volume between days 7 and 10 as shown in FIG. 1. Young nude athymic mice lack an immune system and the older nude mice (as used herein) have an impaired immune system, but have high natural killer cell activity. Thus, it appears that the MOFP-H affects the post-immune response to the tumor.

TABLE I

Tumor Volume Before and After Treatment and Drainage of Fluid.

| Tumor type | Trt. | Tumor Volume Pre-trt. (cm³) | Tumor Vol. 1 day post trt. (cm³) | Tumor Volume 6 days post-trt. | % volume change (6d) | Volume after Drainage (6d) |
|---|---|---|---|---|---|---|
| DMBA/rat mammary | 100 μg MOFP-A | 2.57 | 1.22 | 0.02 | −99 | |
| DMBA/rat mammary | 100 μg MOFP-A | 1.02 | 0.61 | 0.07 | −93 | |
| DMBA/rat mammary | 100 μg MOFP-A | 1.02 | 0.45 | 0.00 | −100 | |
| DMBA/rat mammary | 100 μg MOFP-A | 0.22 | 0.09 | 0.09 | −59 | |
| DMBA/rat mammary | 100 μg MOFP-A | 0.91 | 0.45 | 0.14 | −85 | |
| DMBA/rat mammary | 100 μg MOFP-A | 3.05 | 1.95 | 1.44 | −53 | 0.45 |
| DMBA/rat mammary | 100 μg MOFP-A | 0.22 | 0.22 | 0.10 | −55 | 0.09 |
| DMBA/rat mammary | 100 μg MOFP-A | 0.61 | 0.07 | 0.20 | −67 | 0.19 |
| DMBA/rat mammary | 100 /Ag MOFP-A | 3.88 | 1.44 | 0.45 | −88 | 0.38 |
| DMBA/rat mammary | 100 μg MOFP-A | 0.70 | 0.32 | 0.09 | −87 | 0.00 |
| DMBA/rat mammary | 100 μg MOFP-A | 0.91 | 0.27 | 0.10 | −89 | 0.00 |
| DMBA/rat mammary | 100 μg MOFP-A | 4.51 | 2.35 | 2.14 | −53 | 0.65 |
| DMBA/rat mammary | 100 μg MOFP-A | 2.42 | 2.42 | 0.75 | −69 | 0.18 |
| DMBA/rat mammary | 165 μg MOFP-A | 0.80 | 0.58 | 0.45 | −44 | |
| DMBA/rat mammary | 100 μg MOFP-A | 3.05 | 2.57 | 1.95 | −36 | |
| DMBA/rat mammary | 100 μg MOFP-A | 1.02 | 1.44 | 1.15 | +9 | |
| DMBA/rat mammary | 100 μg MOFP-A | 0.45 | 0.27 | 0.09 | −80 | |
| DMBA/rat mammary | 100 μg MOFP-A | 0.32 | 0.27 | 0.09 | −72 | |
| DMBA/rat mammary | 165 μg MOFP-A | 1.95 | 0.82 | 0.82 | −58 | |
| DMBA/rat mammary | 165 μg MOFP-A | 0.53 | 0.25 | nd | — | |
| DMBA/rat mammary | 165 μg MOFP-A | 0.45 | 0.20 | nd | — | |
| DMBA/rat mammary | 165 μg MOFP-A | 1.18 | 0.10 | 0.10 | −92 | |
| DMBA/rat mammary | 165 μg MOFP-A | 1.05 | 0.32 | 0.32 | −70 | |
| DMBA/rat mammary | 165 μg MOFP-B | 0.55 | 0.30 | 0.30 | −45 | |
| DMBA/rat mammary | 165 μg MOFP-B | 0.12 | 0.00 | 0.00 | −100 | |
| DMBA/rat mammary | 165 μg MOFP-B | 6.35 | 6.50 | 3.8 | −40 | |
| DMBA/rat mammary | 165 μg MOFP-B | 0.45 | 0.10 | 0.00 | −100 | |
| DMBA/rat mammary | 150 μg MOFP-B | 5.58 | 4.03 | 2.81 | −50 | |
| DMBA/rat mammary | 150 μg MOFP-B | 2.81 | 1.95 | 1.26 | −55 | |
| DMBA/rat mammary | 150 μg MOFP-B | 2.25 | 1.95 | 0.65 | −71 | |
| DMBA/rat mammary | 150 μg MOFP-B | 3.45 | 2.35 | 1.60 | −54 | |
| DMBA/rat mammary | 165 μg MOFP-B | 0.35 | 0.07 | 0.00 | −100 | |
| DMBA/rat mammary | 165 μg MOFP-B | 0.66 | 0.39 | 0.40 | −39 | |
| DMBA/rat mammary | 165 μg MOFP-B | 0.32 | 0.13 | 0.06 | −81 | |
| DMBA/rat | 165 μg | 3.05 | 1.77 | 3.05 | 0 | |

TABLE I-continued

Tumor Volume Before and After Treatment and Drainage of Fluid.

| Tumor type | Trt. | Tumor Volume Pre-trt. (cm³) | Tumor Vol. 1 day post trt. (cm³) | Tumor Volume 6 days post-trt. | % volume change (6d) | Volume after Drainage (6d) |
|---|---|---|---|---|---|---|
| DMBA/rat mammary | MOFP-B 165 μg | 1.60 | 0.60 | 0.44 | −73 | |
| DMBA/rat mammary | MOFP-B 165 μg | 2.46 | 1.36 | 0.25 | −90 | |
| DMBA/rat mammary | MOFP-B 165 μg | 1.42 | 0.26 | 0.22 | −85 | |
| DMBA/rat mammary | MOFP-B 165 μg | 2.57 | 1.95 | 0.75 | −71 | |
| DMBA/rat mammary | MOFP-B 165 μg 1 | 8.80 | 6.30 | nd | — | |
| DMBA/rat mammary | MOFP-B 165 μg | 0.20 | 0.00 | nd | — | |
| DMBA/rat mammary | MOFP-B 165 μg | 5.58 | 4.03 | 2.81 | −50 | |
| DMBA/rat mammary | MOFP-B 165 μg | 2.81 | 1.95 | 1.86 | −34 | |
| DMBA/rat mammary | MOFP-B 150 μg | 2.25 | 1.95 | 0.65 | −71 | |
| DMBA/rat mammary | MOFP-B 150 μg | 1.09 | 0.60 | 0.24 | −77 | |
| DMBA/rat mammary | MOFP-B 150 μg | 0.32 | 0.12 | 0.08 | −75 | |
| DMBA/rat mammary | MOFP-B 160 μg MOFP-A + 400 μg rat OFP | 4.20 | 8.2 | 11.0 (2d) | +161 (2d)* | |
| DMBA/rat mammary | 10 μg TNFα | 2.30 | 3.35 | 7.80 | +239 | |
| DMBA/rat mammary | Anti-urease mAb | 1.83 | 2.26 | 4.94 (3d) | +170 (3d)* | |
| DMBA/rat mammary | Anti-urease mAb | 2.24 | 4.35 | 6.79 | +203 | |
| DMBA/rat mammary | Anti-urease | 1.68 | 1.95 | 3.31 | +97 | |
| DMBA/rat mammary | Anti-urease mAb | 0.96 | 1.29 | 2.70 | + | |
| DMBA/rat mammary | Anti-urease mAb | 4.25 | 6.00 | 8.81 | +107 | |
| DMBA/rat mammary | Anti-$T_2$ Toxin mAb | 0.38 | 0.41 | 0.70 | | |
| DMBA/rat mammary | Anti-$T_2$ Toxin mAb | 1.36 | 1.63 | 2.04 | +50 | |
| DMBA/rat mammary | Anti-$T_2$ Toxin mAb | 0.95 | 1.15 | 2.80 | +195 | |
| DMBA/rat mammary | Anti-$T_2$ Toxin mAb | 0.14 | 0.32 | 0.35 | +150 | |
| DMBA/rat mammary | Anti-$T_2$ Toxin mAb | 1.36 | 1.44 | 2.80 | +106 | |
| Rat hepatoma 7777 (transplant) | 170 μg MOFP-B | 5.00 | 0.26 | 3.0 | −40 | |
| Rat hepatoma 7777 (transplant) | 170 μg MOFP-B | 3.80 | 0.25 | 3.5 | −8 | |

TABLE I-continued

Tumor Volume Before and After Treatment and Drainage of Fluid.

| Tumor type | Trt. | Tumor Volume Pre-trt. (cm³) | Tumor Vol. 1 day post trt. (cm³) | Tumor Volume 6 days post-trt. | % volume change (6d) | Volume after Drainage (6d) |
|---|---|---|---|---|---|---|
| Rat hepatoma 7777 (transplant) | 170 µg MOFP-B | 3.70 | 0.20 | 3.8 | 0.0 | |
| Rat hepatoma 7777 (transplant) | 170 µg MOFP-B | 2.9 | 0.18 | 3.8 | +31 | |
| Human (MCF-7) mammary adenocarinoma in nude mouse | 10 µg MOFP-A | 0.33 | 0.21 | 0.21 | −36 | | trt - treatment
nd - no data
*Measurement done at 2 days or 3 days rather than 5–6 due to rapid tumor growth.
Antiurease and anti $T_2$ toxin were administered at a dosage of 100 µg.

TABLE 2

MRI Size Determinations of Anti-OFP Monoclonal Antibody-Treated Rats with DMBA-induced Mammary Carcinomas Tumor Size in sq cm

| Rat # & Treatment | Tumor # | 1 Day pre-trt | 1 Day post-trt | 6 Days 0/0 change post-trt |
|---|---|---|---|---|
| 93-244 | 1 | 1.98 | 1.38 | 1.23 (−38%) |
| MoAb A | 2 | 1.85 | 0.55 | 0.60 (−68%) |
| 5 µg | 3 | 10.27 | 9.66 | 9.89 (−6%) |
| | 4 | 2.01 | 1.60 | 1.09 (−46%) |
| 93-246 | 1 | 5.47 | 14.47 | 4.04 (−72%) |
| MoAb A | 2 | 2.70 | 1.05 | 0.00 (−100%) |
| 5 µg | 3 | 4.04 | 12.73 | 1.19 (−91%) |
| 93-245 | 1 | 14.12 | 14.47 | 13.21 (−94) |
| MoAb A | 2 | 1.75 | 2.01 | 1.35 (−33%) |
| 5 µg | 3 | 1.68 | 1.47 | 0.98 (−42%) |
| 93-247 | 1 | 0.30 | 1.30 | 1.20 (+300%) |
| Control | 2 | 1.55 | 1.82 | 4.71 (+204%) | trt - treatment

Tissue Culture Evaluation

OFP is produced by and released from several cancer cell lines in culture. OFP is present in the cytoplasm of cancer cells and is secreted by the cancer cells.

Rat Hepatoma Cells

Rat hepatoma cells of the cell line MCA-RH 7777 obtained from American Type Culture Collection, Rockville, Md., which is a pure cell line lacking lymphocytes, were grown in Dulbecco Modified Eagles Medium with high glucose and enriched with 0.005M sodium pyruvate, 0.2 U/ml insulin, vitamins, 0.1 mM non-essential amino acids and 15% fetal bovine serum. Cells were continuously grown in either the absence of MOFP-A or presence of MOFP-A at about 2.0 to 10 µg per culture. Cells were fed twice a week with fresh medium until confluent, at which time they were subpassaged by trypsinization. Following trypsinization, cells were counted with a hemocytometer and their viability assessed by trypan blue exclusion. When cells were grown in either the absence of MOFP-A or the presence of 2.0 to 10 µg of MOFP-A, there were no significant differences in the viability or number of cells. This lack of effect of MOFP-A on the growth of rat hepatoma cells indicates that lymphocytes are required for MOFP to reduce the size of rat hepatomas in vivo.

Human Mammary Adenocarcinoma Cells

Figure 2:
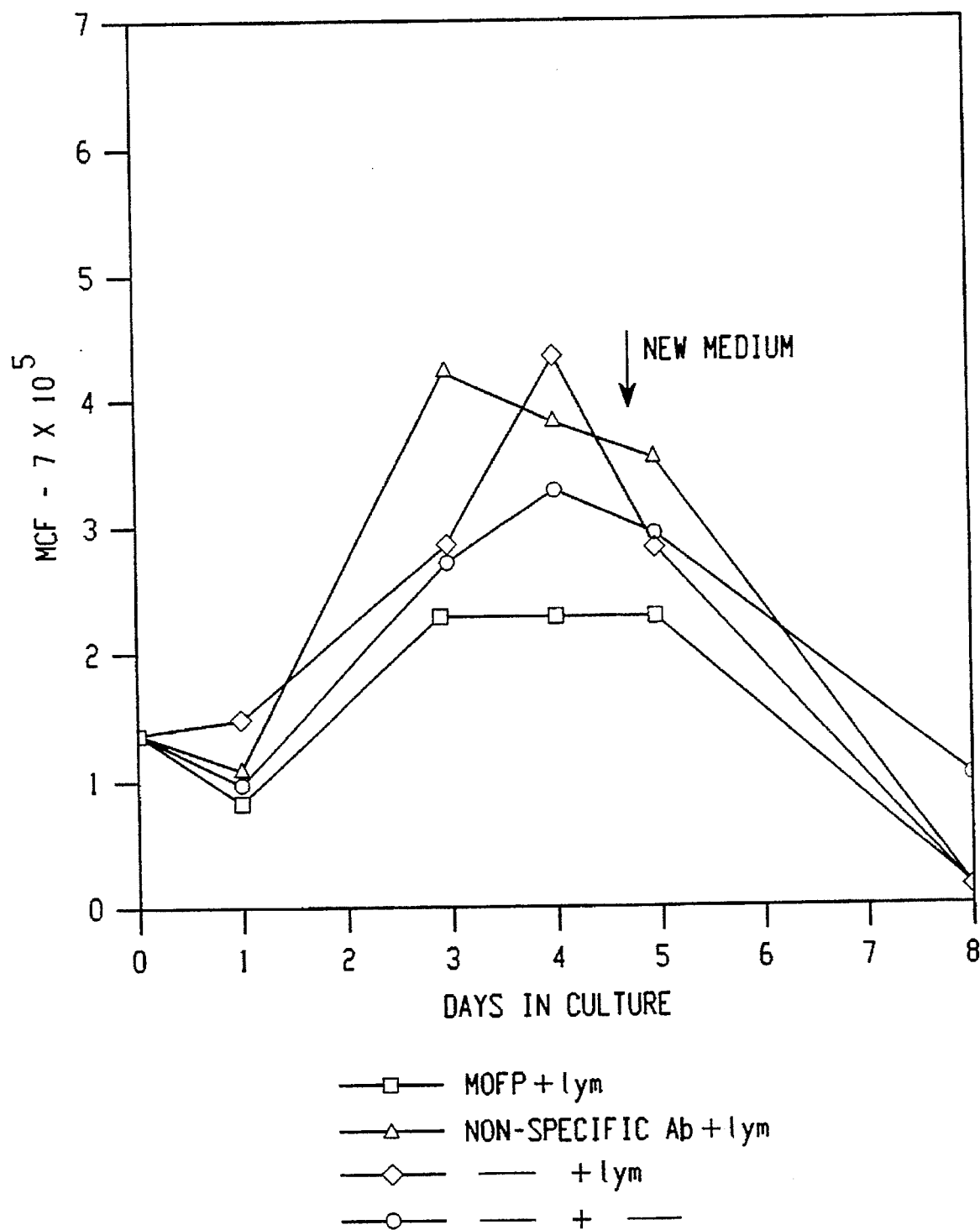
FIG. 2 is a graph showing the effects of anti-human OFP monoclonal antibody and the non-specific monoclonal antibody alpha T2 on the growth rate of MCF-7 human mammary adenocarcinoma cells grown in culture in the presence and absence of lymphocytes.

The human mammary adenocarcinoma cell line MCF-7 was grown in Minimal Essential Medium, Earle's Base, supplemented with 1.0 mM non-essential amino acids, 2.0 mM glutamine, 10% fetal bovine serum, penicillin-streptomycin and fungizone. Cells were plated at a concentration of $1.4 \times 10^5$ cells/well. Either the human MOFP-HIA9 was added at a concentration of about 1.0 mg/ml, or for comparison a nonspecific mAb alpha T2 was added at a concentration of about 1.0 mg/ml was added to representative cultures of MCF-7 cells. Twenty-four hours later, human peripheral blood mononuclear cells obtained from cancer free patients and purified from blood by centrifugation through Ficoll were added to each MCF-7 cell culture, except the controls, at a ratio of 1:5. The human peripheral blood mononuclear cells include lymphocytes. After four days in culture, one-half the medium was replenished with fresh medium containing the same amount of monoclonal antibody added to the culture on day one. Cell viability was determined by trypan blue exclusion of MCF-7 cells removed from the wells by trypsinization. As shown in FIG. 2, the number of viable MCF-7 cells in cultures containing both lymphocytes and MOFP-H was consistently lower than in untreated cultures or in cultures grown in the presence of peripheral blood mononuclear cells and non-specific monoclonal antibody.

Studies, in which monoclonal antibody was not added to the cultures of MCF-7 cells and in which the ratio of lymphocytes to MCF-7 cells was significantly increased to 1:2, showed that this presence of excess lymphocytes significantly depressed the number of viable MCF-7 cells at all time periods. Pre-incubation of the lymphocytes with OFP for 1 hour prior to addition to the cultures reversed this depression particularly during the earlier time periods. These results demonstrate that at an extremely high concentration, peripheral blood mononuclear cells alone can inhibit growth of MCF-7 cells and that this inhibitory effect is overcome by the presence of OFP. This suggests that monoclonal antibodies to OFP inhibit tumor cell growth indirectly, that is, through peripheral blood mononuclear cell activity.

Human Leukemia Cells

Figure 3:
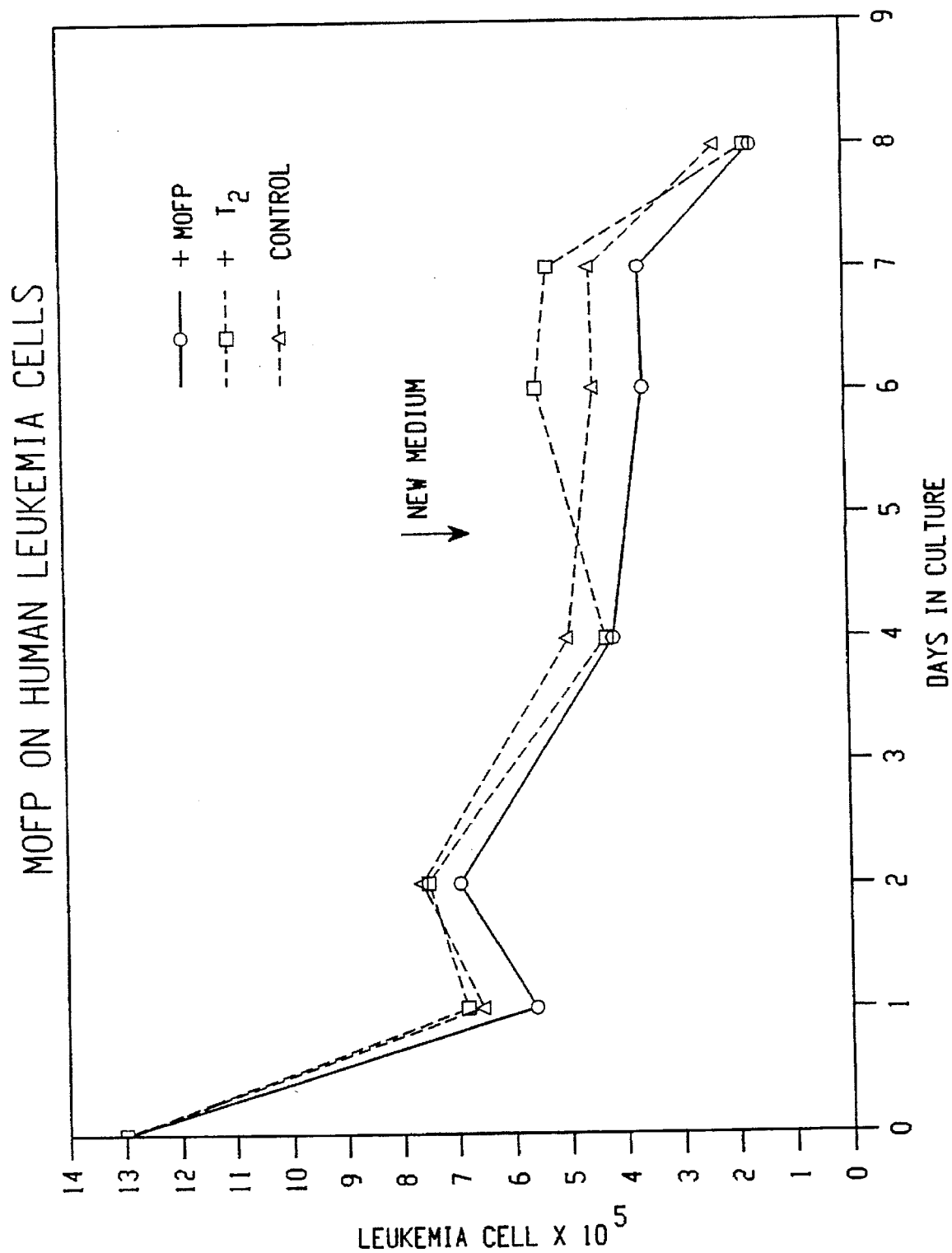
FIG. 3 is a graph showing the effects of anti-human OFP monoclonal antibody and the non-specific monoclonal antibody alpha T2 on human leukemia cells cultured in the presence of lymphocytes.

Human leukemia cells and lymphocytes were isolated simultaneously from the blood of a patient with chronic myelogenous leukemia by centrifugation in a swinging bucket rotor at 1760 rpm for 40 min through a 7 ml gradient of Ficoll from Pharmacia, Piscataway, N.J. The differential cell count of the blood sample showed 64% blast cells and 22% lymphocytes. The buffy coat, that is, the band containing both leukemia cells and peripheral blood mononuclear cells was removed, washed by centrifugation at 2000 g from a balanced salt solution, and seeded at a concentration of $1.3 \times 10^6$ cells per well in RPMI 1640 medium supplemented with 20% fetal bovine serum, glutamine, pyruvate, penicillin-streptomycin and fungizone. On each day following seeding, the cells were counted in a hemocytometer using a light microscope, and viability was assessed by trypan blue exclusion. When the number of leukemia cells in each well reached $13 \times 10^5$, either the MOFP-HIA9 of the present invention or the non-specific monoclonal antibody, alpha T2 from Sigma Chemical Co., St Louis, Mo., were added to the medium at a concentration of 1.0 µg/ml. A control culture of leukemia cells and peripheral blood mononuclear cells was grown in the absence of either monoclonal antibody. New medium containing the same concentration of monoclonal antibody was added to each culture four days later. During the eight days following addition of monoclonal antibody, the number of viable leukemia cells in each of the cultures decreased. However, as shown in FIG. 3, the number of viable leukemia cells in the cultures treated with MOFP-HIA9 was typically lower than the number of viable leukemia cells grown with either no monoclonal antibody or with non-specific monoclonal antibody.

Rat Leukemia Cells

Figure 4:
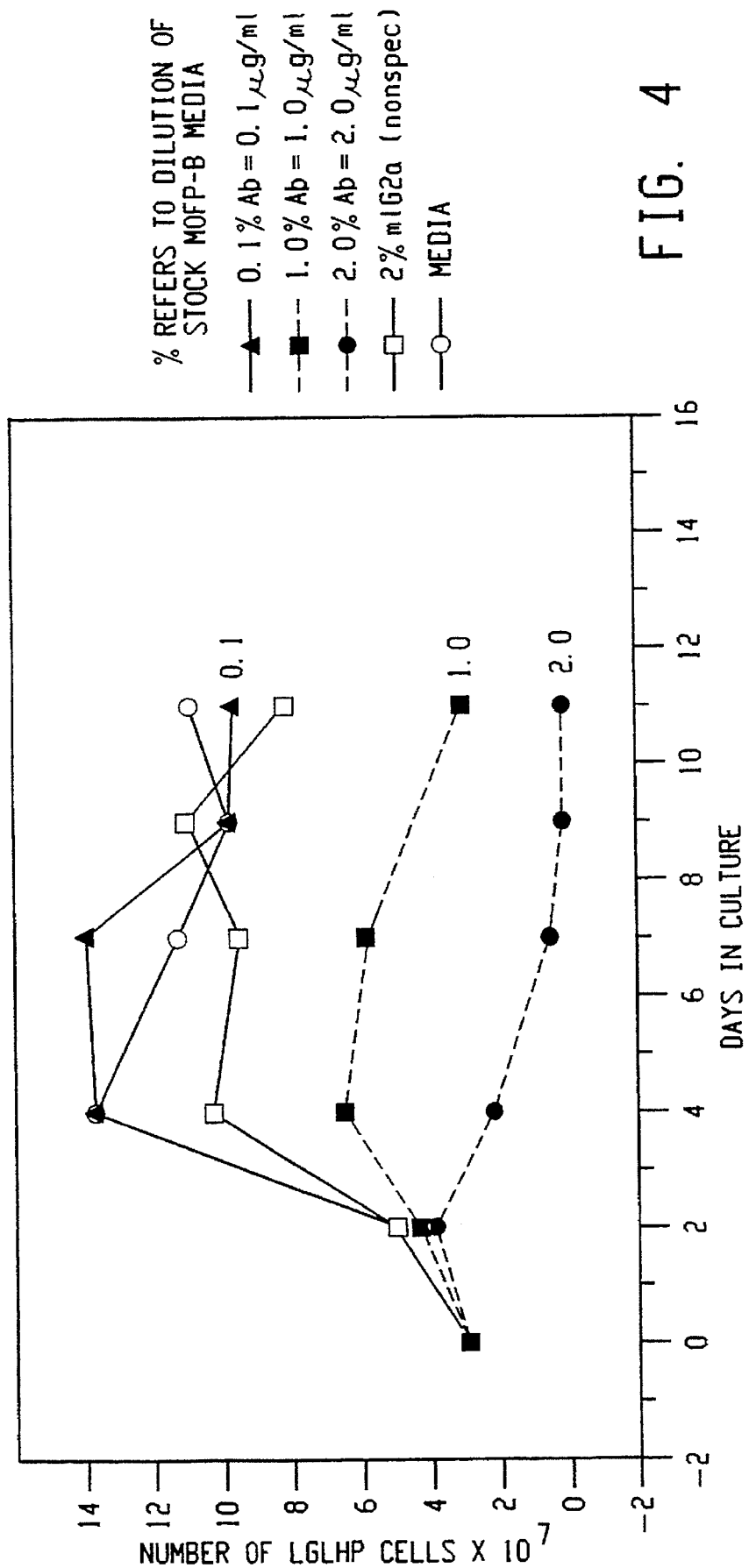
FIG. 4 is a graph showing the effect of anti-rat OFP monoclonal antibody on the growth rate of rat leukemia cells g own in culture in the presence of lymphocytes.

Freshly isolated rat leukemia cells were isolated from Sprague-Dawley strain rats according to the method of P. C. Stromberg, et al., Leukemia Res. 15:427–433, 1991, and cultured in RPMI-1640 media (+20% fetal bovine serum+ additives), at a concentration of about $1.0 \times 10^7$ cells/mi. This method of isolation does not separate the leukemia cells from the macrophages and lymphocytes present in the rat blood. Either about 0.1 µg/ml, about 1.0 µg/ml or about 2.0 µg/ml of MOFP-B was added to the cultures. No MOFP-B was added to the control. As shown in FIG. 4, the concentration of the rat leukemia cells that were either not exposed to MOFP-B, or only received 0.1 µg/ml MOFP-B, increased. However, a 1 µg dose of MOFP-B significantly inhibited cell growth. The inhibition of cell growth was more pronounced with the 2 µg dosage which decreased the cell concentration shortly after the MOFP-B was added to the cultures.

The monoclonal antibodies against OFP are effective in treating cancer.

Diagnostic Tests

In addition to treating cancers, the monoclonal antibody against OFP is also useful in diagnostic tests, particularly as a diagnostic test for cancer. The immunobioassay and a modified ELISA, which employ monoclonal antibodies to OFP, are useful for detecting OFP in a sample such as blood, and are therefore useful in detecting cancer in patient.

Immunobioassay

The immunobioassay relies on the ability of the monoclonal antibodies to OFP to bind OFP and remove the detectable OFP from solution by immunoprecipitation. The immunobioassay is used to detect OFP in suspected cancer patients and in fractions eluted from fractionation columns. An aliquot of each patient sample was incubated for 2 hours at 4° C. with the appropriate monoclonal antibody, that is, the anti-rat OFP monoclonal antibodies or anti human OFP monoclonal antibody insolubilized on anti-mouse IgG agarose beads from Sigma Chemical Co., St. Louis, Mo. Anti-rat OFP MOPFP-E or Anti-human OFP MOPFP-HIA9 were used against human samples, Anti-rat OFP MOPFP-E and Anti-rat OFP MOPFP-C were used against canine samples.

The agarose bead anti-mouse (IgG(H+L))-MOFP complex was prepared by first washing the agarose beads with binding buffer containing 0.01M phosphate buffer, (pH 7.2), and 0.25M NaCl and then incubating the beads with the monoclonal antibody to OFP for 18 hours at 4° C. in the same buffer. The beads were sedimented by centrifugation for 30 seconds at 16,000× g in a microfuge and non-specific sites were blocked by incubation with 2% non-fat dry milk in 0.5M NaCl-TMK for 30 minutes at 4° C. After blocking, the beads were washed 3 times in 0.5M NaCl-TMK and resuspended in an equal volume of the same buffer. 20 µl of the agarose bead-monoclonal antibody complex were then incubated with each 250 µl of the patient test sample for 2 hours at 4° C. Any OFP present in the patient test sample was bound by the OFP monoclonal antibody on the beads. The bead complex, now with OFP bound, was removed by centrifugation for 30 seconds at 16,000× g. The supernatant was tested for OFP activity in the bioassay as described below. Control samples were treated with blocked beads that lacked the OFP monoclonal antibody and tested for OFP activity in the bioassay.

Bioassay

The Bioassay is used both to detect OFP in a sample from suspected cancer patients, as well as to detect OFP in laboratory samples particularly eluted fractions from separation columns.

The bioassay is a cell free system designed to measure the release of RNA from isolated nuclei. First, cytosol proteins are isolated from, for example, rats. Male Sprague-Dawley rats from Harlan Sprague-Dawley, Indianapolis, Ind., weighing approximately 250 g were fasted overnight. Following euthanasia by ether anesthesia and exsanguination, the livers were perfused with 10 ml of 0.25M sucrose and then dissected out and homogenized by 6 strokes of a Dounce homogenizer of 0.25M sucrose-TMK which contained 50 mM Tris-Cl (pH 7.5); 2.5 mM $MgCl_2$; and 25 mM KCl. 2 ml sucrose-TMK was used per gram of wet weight liver. The homogenate was centrifuged for 10 minutes at 12,000× g in a Beckman JA-20 rotor and the resulting supernatant was centrifuged for 90 minutes at 105,000× g in a Beckman Ti50 rotor. The final supernatant, that is the cytosolic fraction, was removed and dialyzed overnight at 4° C. against TMK buffer. After dialysis, the dialyzed cytosol protein was removed and retained for subsequent use as described below.

Next, labeled nuclei or more specifically labeled nuclear RNA was prepared. Liver nuclear RNA was pre-labelled in vivo by injecting intraperitoneally an ether anesthetized male Sprague-Dawley rat with 100 microCuries ($^3$H) orotic acid. After a 30 minute labeling time, the rat was euthanized by ether anesthesia and exsanguination and the liver removed following perfusion with 10 ml of a solution containing 0.25M sucrose and 3.3 mM calcium acetate. The liver tissue was homogenized in 2.3M sucrose, 3.3 mM calcium acetate (15 ml per gram wet weight liver) by 4 strokes of a Dounce homogenizer using a loose fitting pestle with more than usual clearance. The resulting homogenate was centrifuged at 34,000× g for 60 minutes at 4° C. The pelleted nuclei were rinsed with a solution containing 1M sucrose, 1 mM CaOAc (1.5 ml/g original liver) and resuspended in the same at 1 ml/g.

Next, a cell free medium was prepared; the cell free medium contained: $5\times10^6$ of the prelabeled nuclei per ml; 5 mg/ml of the dialyzed cytosol protein; 50mM Tris-Hcl (pH 7.5); 25 mM KCl; 2.5 mM $MgCl_2$; 0.5 mM $CaCl_2$; 0.3 mM $MnCl_2$; 5.0 mM NaCl; 2.5 mM phosphoenolpyruvate; 35 units/ml pyruvate kinase; 2.5 mM $Na_2HPO_4$; 5.0 mM spermidine; 2.0 mM dithiothreitol; 2.0 mM ATP; 300 μg/ml low molecular weight yeast RNA; 0.4 mg/ml methionine; 0.3 mM GTP; and 170 mM sucrose.

Since the cell free medium contains limited RNA transport factors, it responds to the addition of exogenous RNA transport factors, such as the OFP present in a sample from a cancer patient. An aliquot of up to 100 μl of the patient sample such as blood plasma/tissue cytosol or 200 μl of a column fraction to be tested, was added to 1 ml of the cell free medium and incubated at 30° C. for 30 minutes. The nuclei were pelleted by centrifugation at 1050× g for 10 minutes and the resulting supernatant decanted into fresh tubes containing 100 μl of 50% trichloroacetic acid. The samples were vortexed briefly and the resultant precipitate, which contains protein and RNA, was allowed to stand at 0° C. for 10 minutes before pelleting at 1050× g for 10 minutes. The pellets were washed with 1 ml cold 100% ethanol to remove excess water and trichloroacetic acid, and were solubilized by digestion with 0.4 ml Unisol from Isolab, Akron, Ohio, for 20 minutes at 40° C. The solubilized samples were mixed with 200 μl methanol and then added to 9 ml Unisol Complement from Isolab, Akron, Ohio, scintillation fluid and the counts per minute (cpm) $^3H$ measured in a scintillation counter. One unit of activity in the bioassay is defined as the energy (ATP) and OFP-dependent transport of one percent of the nuclear counts in messenger-like RNA during a 30 minute incubation. OFP activity was expressed as percent of the total counts transported per milligram exogenous protein added to the assay mix as calculated in the formula:

$$\frac{\frac{cpm \ transported}{transported}}{\frac{cpm \ from \ equal \ \# \ nuclei}{mg \ protein \ added}} \times 100 = \frac{\% \ labelled \ RNA}{milligram \ protein \ added}$$

The activity due to the OFP in a patient sample was determined by subtracting the RNA transport activity in the aliquot of sample treated with MOFP, from the RNA transport activity in an aliquot of patient sample not exposed to MOFP. There was sufficient monoclonal antibody in each assay to bind 2.0 μg of OFP, which significantly exceeded the amount of OFP in any samples assayed. This assay shows excellent linearity with OFP concentration in pure or impure preparations of OFP.

Detection of Cancer Using ELISA Tests

Competitive ELISA

First, 96 well polystyrene ELISA plates were coated with 30 ng/100 ul/well of purified human OFP in coating buffer, containing 0.1M sodium bicarbonate in phosphate buffered saline, having a pH of 9.6, at 4° C. overnight. The residual binding sites were blocked with 300 μl/well of 1% bovine serum albumin in phosphate buffered saline at room temperature for 1 hour. Next, 50 μl of the sample to be assayed and 50 μl of a monoclonal antibody to OFP, for example MOFP-HIC8, were added to each well (diluted in 1% bovine serum albumin in phosphate buffered saline). The plates were incubated at room temperature for 1 hour. The plates were washed five times with wash buffer containing 0.05% Tween 20 in phosphate buffered saline. Next, 100 μl/well of a anti-mouse IgG-horseradish peroxidase conjugate, was added to each well. The anti-mouse IgG-horseradish peroxidase conjugate was diluted 1:2000 in 1% bovine serum albumin in phosphate buffered saline. The plates were incubated at room temperature for 1 hour. The plates were washed five times with wash buffer. Next, 100 μl/well of substrate (containing 0.5 mg/ml o-phenylenediamine (OPD) in 25 mM citrate/50 mM $N_2HPO_4$, pH 6.0 and 0.015% $H_2O_2$ was added to the wells and incubated at room temperature for 20 minutes in the dark. The reaction was stopped by adding 50 μl/well of 4.5M $H_2SO_4$. The optical densities were read by using EIA reader at a wavelength of 492 nm.

Direct ELISA

Samples of normal plasma and cancer patient-plasma were diluted 1:1 with phosphate buffered saline. One volume of mixture was added to centricon-10 filter having a 10 kd molecular weight cut off and centrifuged at 5000G (7000 rmp) for 1 hour. One volume of PBS was added to retentate and centrifuged for 30 min. The final dilution was about 1:3. The plate wells were then coated with retentate at 1:6, 1:12, 1:24, 1:48 and 1:96 final dilution in bicarbonate coating buffer, having a pH 9.6 overnight at 4° C. The plates were washed 2 times with wash buffer containing 5% Tween 20 in phosphate buffered saline. Residual binding sites were blocked with 4% bovine serum albumin, 300 μl/well for 2 hours. The plates were washed 2 times with wash buffer. Next, 100 μl of a monoclonal antibody to OFP, for example, MOFP-HIB7 at 1:200 dilution in 1% bovine serum albumin was added to the wells and incubated for 1 hour with agitation. The plates were washed 5 times with wash buffer. Next, 100 μl horseradish peroxidase conjugated goat anti-mouse IgG was added at 1:2000 dilution to each well, and incubated for 1 hour. The plates were washed 5 times with wash buffer. Next, 100 μl/well of substrate containing 5 μg OPD & 5 μl $H_2O_2$/10 ml citrate-phosphate buffer was added to each well and incubated for 5 minutes. The enzyme reaction was stopped by adding 50 μl/well 2M $H_2SO_4$. The absorbance of light was measured at 492 nm in an EIA reader.

Use of the Monoclonal Antibodies to OFP to Detect Cancer

Detection of Breast Cancer using Anti-Human OFP Monoclonal Antibodies

In a blind study, the anti-human OFP monoclonal antibody, M-OFPHA9, was used in immunobioassay to determine the presence or absence of OFP in plasma samples from breast cancer patients, patients with benign breast disease and from normal controls. The results are summarized below in Table 3.

TABLE 3

DETECTION OF CANCER IN HUMAN PLASMA WITH ANTI-HUMAN OFP MONOCLONAL ANTIBODY

| Patient # | Histopath. of Breast Lesion* | Immunoassay for OFP Result | Actual Value | Predicted OFP Result |
|---|---|---|---|---|
| 1 | Malignant | + | 0.45 | + |
| 2 | Malignant | + | 0.43 | + |
| 3 | Benign | − | 0.08 | − |
| 4 | Benign | − | 0.06 | − |
| 5 | Benign | − | 0.07 | − |
| 6 | Benign | − | 0.00 | − |
| 7 | Benign | − | 0.06 | − |
| 8 | Malignant | + | 0.52 | + |
| 9 | Benign | + | 0.32 | − |
| 10 | Benign | + | 0.36 | − |
| 11 | Benign | + | 0.54 | − |
| 12 | Benign | − | 0.00 | − |
| 13 | Benign | − | 0.08 | − |
| 14 | Benign | − | 0.09 | − |
| Blood Bank Plasma Sample | | | | |
| 6 | Malignant | 6(+) | 0.43* | 6(+) |
| 5 | Controls (Normal) | 5(−) | 0.06* | 5(−) |

*average
*Breast lesions were verified by biopsy.

As can be seen in Table 3, three patients with active breast cancer, that is breast carcinoma, tested positive for OFP using the anti human OFP monoclonal antibody. The levels were over three times control values. Significantly, no OFP was detected in patient #6 who had curative surgery for breast carcinoma in situ and Tamoxifen adjuvant therapy. Eight patients with benign breast disease tested negative for OFP with values approximately equal to those of the controls. Three patients tentatively diagnosed as having benign breast disease, two of which were severe enough to warrant biopsy, tested positive for OFP. Biopsy indicated benign breast disease. Whether these specific cases are false positives, or are due to preneoplastic lesions, or are due to reviewing only a noncancerous portion of the specimen has not been determined. In addition, six plasma specimens, obtained through Ohio State University Tissue Procurement program, from patients with breast carcinoma were positive for OFP, while 5 plasma specimens from OSU tissue procurement from normal controls were negative for OFP. Thus, the immunobioassay is useful as a diagnostic test for the presence of cancer.

Detection of cancer in Dogs using Anti-Rat OFP Monoclonal Antibodies

Anti-rat OFP monoclonal antibodies, MOFP-C and MOFP-E, were used in the immunobioassay to determine the presence or absence of OFP in plasma samples from canine patients, and from normal canine controls. The results are summarized below in Table 4.

TABLE 4

CANCER DETECTION IN CANINE PATIENTS BY IMMUNOBIOASSAY USING ANTI-RAT OFP MONOCLONAL ANTIBODY

| Diagnosis | OFP detected |
|---|---|
| Malignant Neoplasm | |
| Mast cell tumor | + |
| Nasal carcinoma | + |
| Transitional cell carcinoma | + |
| Tonsillar SQ cell carcinoma | + |
| Transitional cell carcinoma | + |
| Malignant lymphoma | + |
| Pancreatic islet cell carcinoma | + |
| Malignant lymphoma | + |
| Malignant Melanoma (oral) | + |
| Chondrosarcoma | − |
| Periorbital carcinoma | − |
| Undifferentiated malignancy | + |
| Neuroendocrine carcinoma | + |
| Squamous cell carcinoma | + |
| Osteosarcoma (femoral) | + |
| Malignant lymphoma | + |
| Mast cell tumor | + |
| *Feline LSA | + |
| Controls | |
| 6 Healthy controls | − |
| Hypothyroidism | − |
| ITP | + |
| Distemper | − |
| Capillary hemangioma (benign) | − |
| AIHA | − |

11 non-malignant controls verified by surgical biopsy
18 malignant neoplasms verified by surgical pathology
A positive result was recoreed where either the MOFP-C or MOFP-E, or both detected OFP in the sample.

As can be seen in Table 4, 16 of 18 samples with active malignancy tested positive for OFP using the anti rat monoclonal antibody of OFP. Only 2 of 18 samples with active malignancy tested negative for OFP using the anti rat monoclonal antibody to OFP. The two false negatives are believed to result from the less specific anti-rat monoclonal antibody. The six healthy controls all tested negative for OFP. Of the controls with non-malignant diseases, 4 out of 5 dogs tested negative for OFP. The single apparent false positive result could be either actual false positive or due to an, as yet, undetected malignancy.

Detection of Human Colon Cancer and Breast Cancer Using Anti-Human OFP Monoclonal Antibodies Three anti-human OFP monoclonal antibodies, MOFP-HA9, MOFP-HB7 and MOFP-HC8 were used in the immunobioassay to detect the presence of OFP in plasma of human colon cancer and breast cancer subjects and control subjects. The results are summarized below in Table 5.

TABLE 5

CANCER DETECTION IN HUMAN PLASMA BY IMMUNOBIOASSAY USING ANTI HUMAN OFP MONOCLONAL ANTIBODIES

| | | OFP Activity µg/mg protein | | |
|---|---|---|---|---|
| Patient # | Tumor Site | MOFP-HA9 | MOFP-HB7 | MOFP-HC8 |
| 1 | Colon | 0.21 | 0.25 | 0.18 |
| 2 | Colon | 0.32 | 0.27 | 0.21 |
| 3 | Colon | 0.19 | nt | nt |
| 4 | Colon | 0.17 | nt | nt |
| 5 | Colon | 0.18 | nt | nt |
| 6 | Colon | 0.25 | nt | nt |

TABLE 5-continued

CANCER DETECTION IN HUMAN PLASMA
BY IMMUNOBIOASSAY USING ANTI HUMAN OFP
MONOCLONAL ANTIBODIES

| | | OFP Activity µg/mg protein | | |
|---|---|---|---|---|
| Patient # | Tumor Site | MOFP-HA9 | MOFP-HB7 | MOFP-HC8 |
| 7 | Colon | 0.41 | nt | nt |
| 1 | Breast | 0.25 | 0.28 | 0.30 |
| 2 | Breast | 0.27 | 0.26 | 0.28 |
| 3 | Breast | 0.16 | nt | nt |
| 4 | Breast | 0.20 | nt | nt |
| 5 | Breast | 0.25 | nt | nt |
| 6 | Breast | 0.30 | nt | nt |
| 7 | Breast | 0.33 | nt | nt |
| 1 | Control | 0 | 0 | 0 |
| 2 | Control | 0 | 0 | 0 |
| 3 | Control | 0 | nt | nt |
| 4 | Control | 0 | nt | nt |
| 5 | Control | 0 | nt | nt |
| 6 | Control | 0 | nt | nt |
| 7 | Control | 0 | nt | nt |

Detection of Ovarian and Prostate Cancer using the Anti-rat OFP Monoclonal Antibody In a blinded study, plasma taken from suspected human ovarian and prostate cancer patients was analyzed according to the immunobioassay with anti rat OFP monoclonal antibody, MOFP-E. The results were compared to other conventional assays and are shown in Tables 6 and 7.

TABLE 6

Detection of Suspected Ovarian and Prostate Cancer with
Anti-Rat OFP Monoclonal Antibody

| | Results of Marker Assays | | | |
|---|---|---|---|---|
| Number of Patients | OFP | PAP | PSA | LASA |
| 3 | + | + | + | + |
| 10 | + | + | + | − |
| 1 | + | − | + | − |
| 10 | − | − | − | − |
| 3 | + | − | − | − |
| 8 | − | + | + | + |
| 1 | − | + | + | − |

PAP - prostatic acid phosphatase
PSA - prostate specific antigen

The anti-rat OFP monoclonal antibody MOFP-E which has moderate specificity for human OFP, performs well in detecting human cancer. Indeed, for prostate cancer the anti-rat OFP monoclonal antibody is comparable to conventional assays such as prostatic acid phosphatase and prostate specific antigen, and out performs the lipid associated sialic acid assay ("LASA"). Similarly results are obtained in detecting human ovarian cancer, as shown in Table 7.

TABLE 7

Detection of Suspected Ovarian Cancer with
Anti-Rat OFP Monoclonal Antibody

| | Results of Marker Assays | | | |
|---|---|---|---|---|
| Number of Patients | OFP | Cal25 | DM/70 | LASA |
| 13 | + | + | + | + |
| 3 | + | + | + | − |
| 10 | − | − | − | − |

TABLE 7-continued

Detection of Suspected Ovarian Cancer with
Anti-Rat OFP Monoclonal Antibody

| | Results of Marker Assays | | | |
|---|---|---|---|---|
| Number of Patients | OFP | Cal25 | DM/70 | LASA |
| 3 | − | + | + | − |
| 6 | − | + | + | + |

As predicted, using the anti-rat monoclonal antibody MOFP-E, which is directed to the carbohydrate moiety of the OFP to detect human cancer resulted in an apparent 25% false negative rate. Nevertheless, for ovarian cancer the anti-rat OFP monoclonal antibody MOFP-E is comparable to conventional assays of mucin type tumor-associated antigens such as Ca125 and Dm70, as well as LASA.

Figure 5:
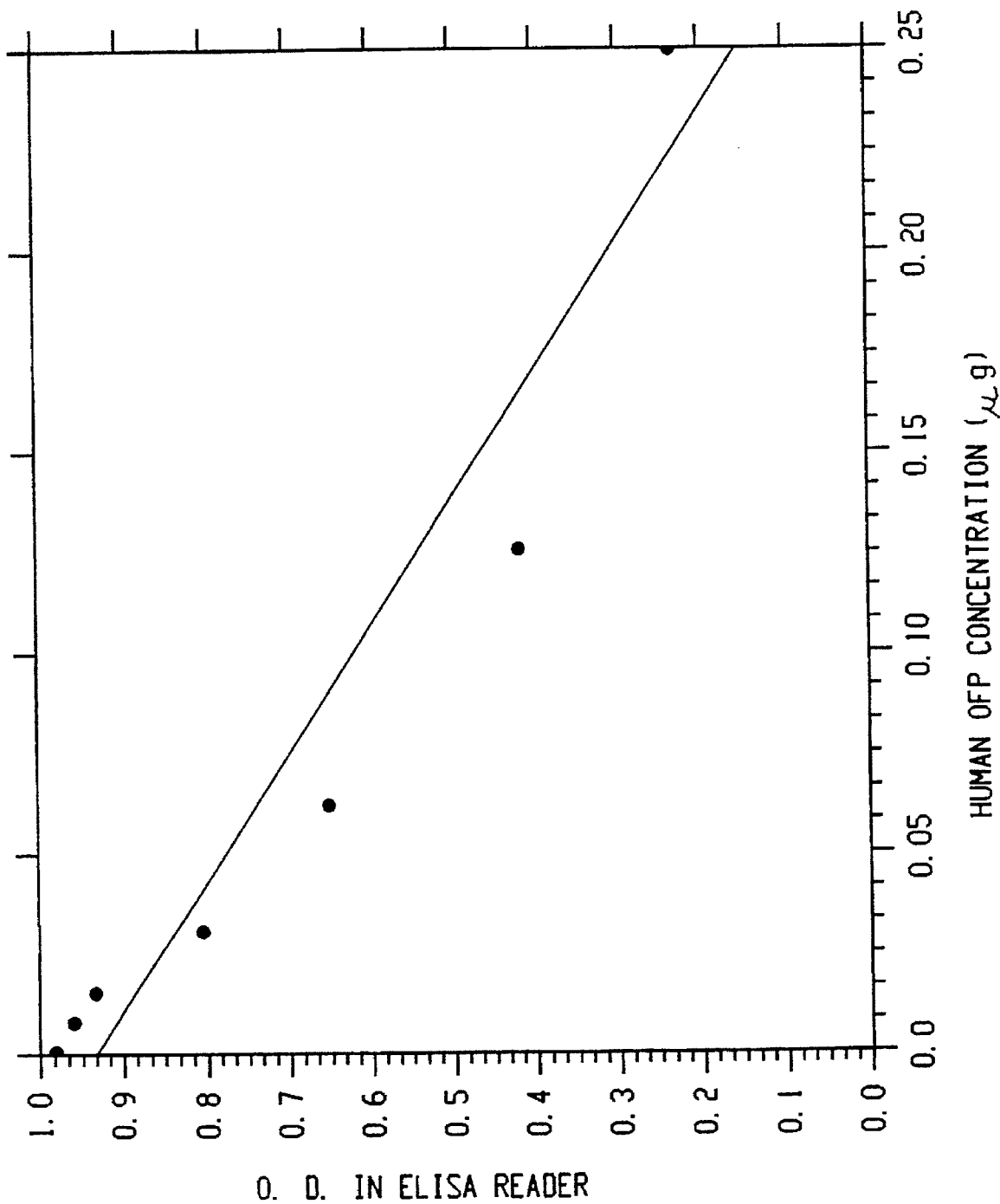
FIG. 5 is a graph showing the relationship between the optical density of Competitive ELISA samples and the concentrate on of known quantities of partially purified human OFP.
Figure 6:
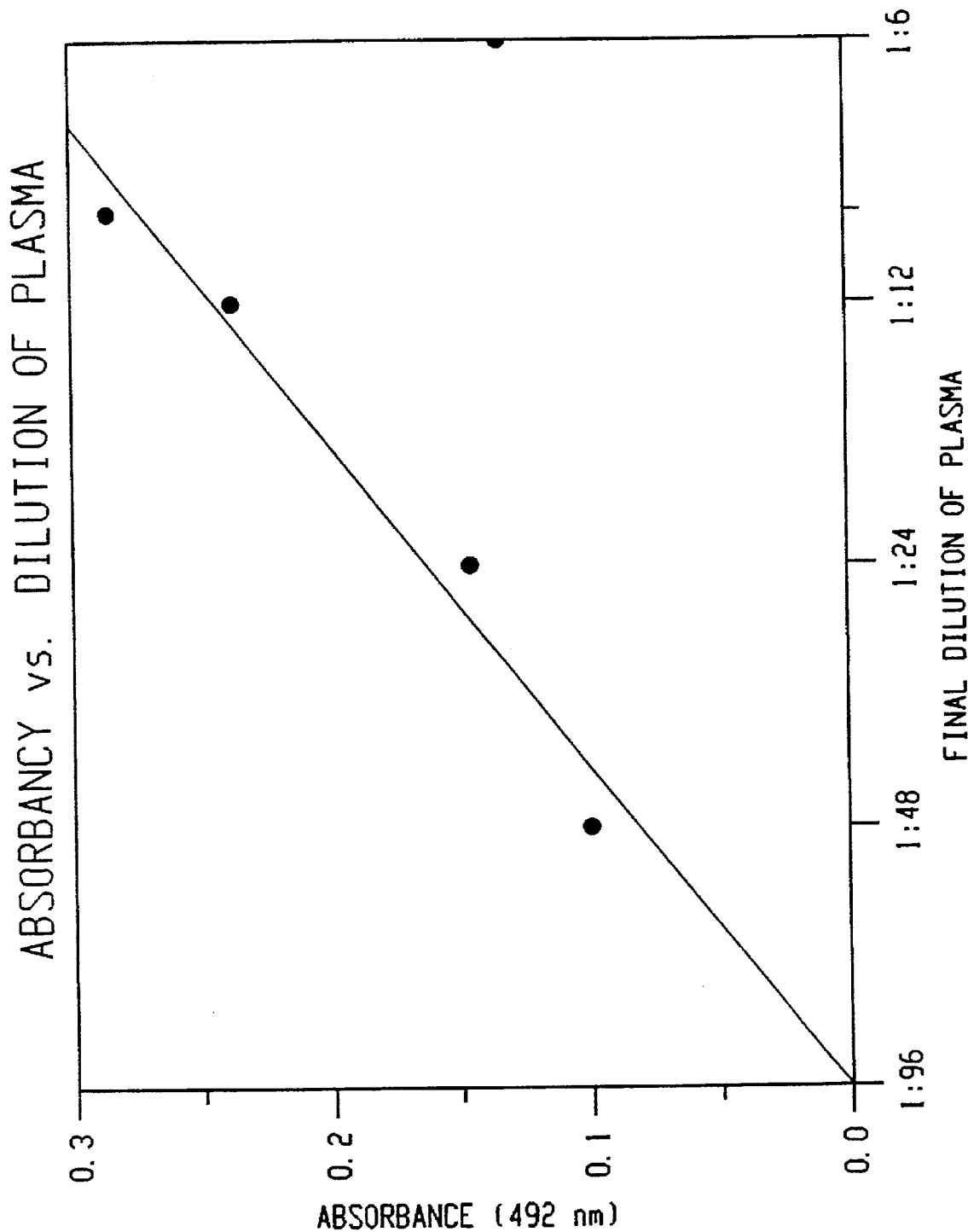
FIG. 6 is a graph showing the relationship between the optical densities of Direct ELISA samples and the dilution of human plasma from a patient with colon cancer.

Detection of Colon Cancer in Human Subjects Using the Direct Elisa and Competitive Elisa The Competitive ELISA test described above and employing the anti-human monoclonal antibody HIA9 was used to determine the correlation between OFP in various dilutions of pure OFP in solution and the measured absorbance values. The results are shown in FIG. 5. Similarly, the direct ELISA test described above and employing the anti-human monoclonal antibody HAI9, was used to determine the correlation between OFP in various dilutions of plasma from a colon cancer patient and the measured absorbance values. The results are shown in FIG. 6.

Detection of Prostate Cancer, Pancreatic Cancer, and Myelogenous Leukemia using Monoclonal Antibodies to OFP The competitive ELISA was used to detect a variety of human cancers. The monoclonal antibody, MOFP-HIC8 was incubated with 100 ng of human plasma, either from a cancer patient or a control. The wells of microtiter plates were coated with 10 ng of human OFP per well. 100 ml of the MOFP-HIC8—sample mixture was added to each well. The results are shown in Table 8.

TABLE 8

DETECTION AND MEASUREMENT OF OFP IN VARIETY
OF HUMAN CANCERS WITH ANTI-HUMAN OFP

| Plasma Source | % Inhibition at a 1:1000 Dilution of Plasma* |
|---|---|
| (1) Non-cancer (normal) | 0 |
| (2) Prostatic carcinoma | 25.2 |
| (3) Acute Myelogenous Leuk. | 35.5 |
| (4) Chronic myelogenous Leuk. | 44.7 |
| (5) Pancreatic cancer | 47.1 |

*Data after substraction of normal (background) value
The concentration of plasma protein in the preincubation mix of plasma plus antibody, which was then added to the well was approx 100 mg/ml.

Detection of Colon Cancer Using the Monoclonal Antibodies

Figure 7:
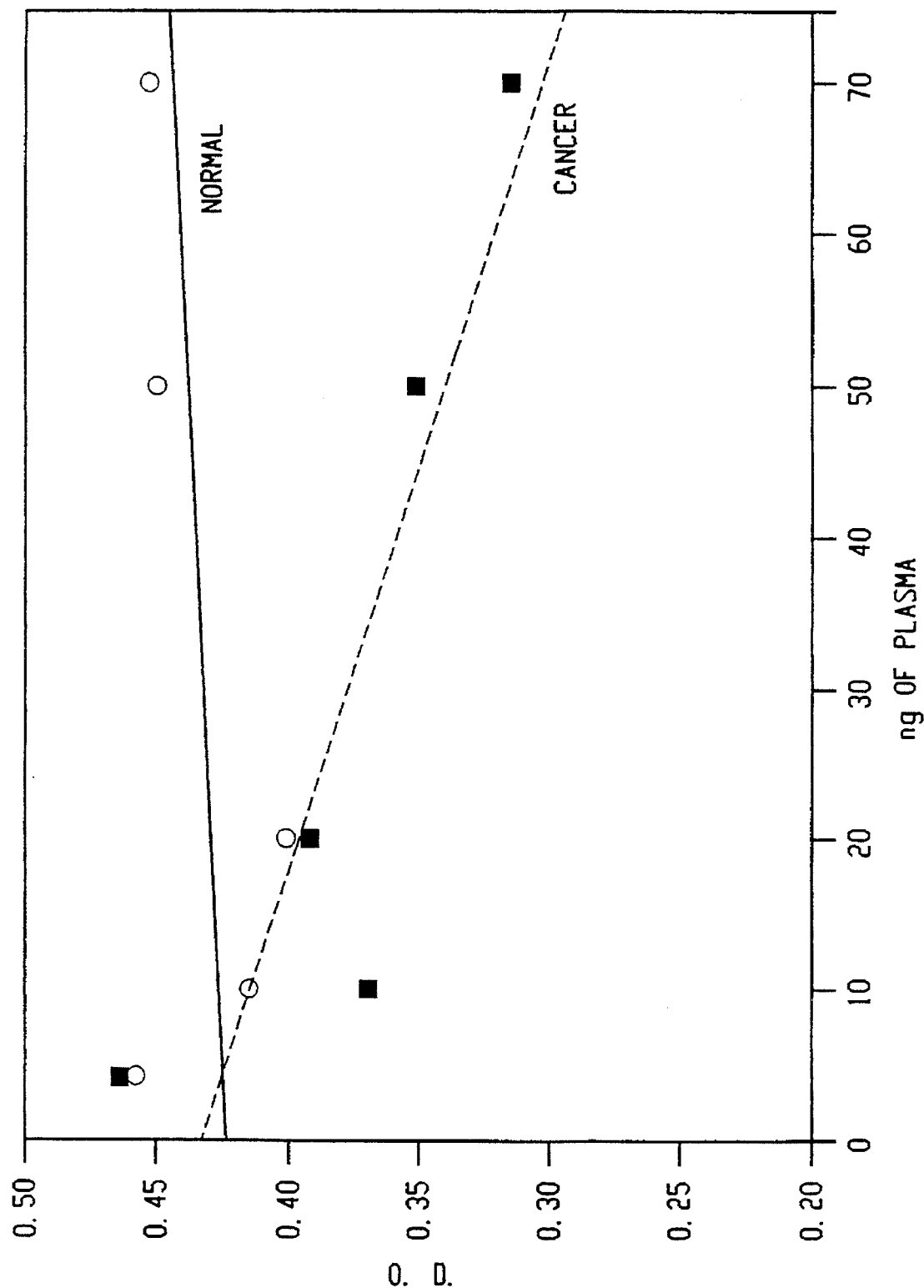
FIG. 7 is a graph comparing the optical densities of Direct ELISA test samples from control subject plasma to human colon cancer subjects plasma. The Direct Elisa employed the anti human monoclonal antibody OFP-IC8.

The competitive ELISA test described above was used to detect human OFP in unfractionated plasma samples from colon cancer patient. The monoclonal antibody, MOFP-HIC8 was incubated with various samples ranging from 0 ng to 70 ng of human plasma, either from a cancer patient or a control. Wells of plates were coated with 10 ng of human OFP per well. Then 100 mg/ml of the MOFP-HIC8—sample mixture was added to each well. The results are shown in FIG. 7.

Detection of Cancer in Dogs using Anti-Canine Monoclonal Antibody

The anti-canine OFP monoclonal antibody MOFP-51C9 was used in the immunobioassay to determine the presence or absence of OFP in plasma samples from canine patients, and from normal canine controls. The results are summarized below in Table 9.

TABLE 9

DETECTION AND MEASUREMENT OF OFP IN VARIETY OF CANINE CANCERS WITH ANTI-CANINE OFP

| Plasma Source | OFP (% transport/mg protein) |
| --- | --- |
| (1) Control (Non-cancer) | 0 |
| (2) Control | 0 |
| (3) Control | 0 |
| (4) Lymphosarcoma | 0.20 |
| (5) Squamous cell carcinoma | 0.16 |
| (6) Mast cell tumor | 0.22 |

As can be seen in Table 9, the anti-canine monoclonal antibody against OFP detects OFP, and thus cancer in canine patients.

The OFP detection tests are useful for the detection of cancer in animals, preferably mammals, more preferably in humans and house pets. The OFP detection tests are also useful for developmental and cancer research in animals including rodents and other experimental animals.

Although certain embodiments of this invention have been shown and described, various adaptations and modifications can be made without departing from the scope of the invention as defined in the appended claims.

We claim:

1. A method for producing a monoclonal antibody which binds to placental oncofetal protein and to tumor-produced oncofetal protein, wherein the placental oncofetal protein and the tumor-produced oncofetal protein are from the same species of mammal comprising the steps of:

a. providing placenta from said species of mammal;

b. extracting placental oncofetal protein from the placenta of step a:

c. purifying the placental oncofetal protein extracted in step b;

d. immunizing an animal with the placental oncofetal protein obtained in step c;

e. obtaining at least one cell from the animal which produces antibody to the placental oncofetal protein of step c; and f. producing a hybridoma using the cell of step e wherein the hybridoma produces antibody that binds to placental oncofetal protein and to tumor-produced oncofetal protein from the same species of mammal.

2. The process of claim 1 wherein the monoclonal antibody binds to human placental oncofetal protein and to human tumor-produced oncofetal protein and wherein the placenta of step a is from a human.

3. A monoclonal antibody produced according to the process of claim 1, wherein said antibody binds to placental oncofetal protein and to tumors-produced oncofetal protein from the same species of mammal.

4. The monoclonal antibody of claim 3 wherein said monoclonal antibody is produced by immunizing an animal with human placental oncofetal protein and wherein the monoclonal antibody binds to human placental oncofetal protein and to human tumor-produced oncofetal protein.

5. The monoclonal antibody of claim 4 produced by a hybridoma having the identifying characteristics of ATCC designation number HB 11565.

6. The monoclonal antibody of claim 4 produced by a hybridoma having the identifying characteristics of ATCC designation number HB 11582.

7. A hybridoma which is produced according to a process comprising the steps of:

a. providing placenta from a species of mammal;

b. extracting placental oncofetal protein from the placenta of step a;

c. purifying the placental oncofetal protein extracted in step b;

d. immunizing an animal with the placental oncofetal protein obtained in step c;

e. obtaining at least one cell from the animal which produces antibody to the placental oncofetal protein of step c; and f. producing a hybridoma using the cell of step e; wherein said hybridoma produces monoclonal antibody that binds to placental oncofetal protein and to tumor-produced oncofetal protein from the same species of mammal.

8. The hybridoma of claim 7 wherein the placenta of step a is from a human and wherein the monoclonal antibody binds to human placental oncofetal protein and to human tumor-produced oncofetal protein.

9. The hybridoma of claim 8 having the ATCC designation number HB 11582.

10. The hybridoma of claim 8 having the ATCC designation number HB 11565.

* * * * *